US010058502B2

(12) United States Patent
Macneill et al.

(10) Patent No.: US 10,058,502 B2
(45) Date of Patent: *Aug. 28, 2018

(54) NAIL POLISH COMPOSITIONS

(71) Applicant: L'OREAL, Paris (FR)

(72) Inventors: Christopher Michael Macneill, Fanwood, NJ (US); XianZhi Zhou, Millburn, NJ (US); Chunhua Li, Hillsborough, NJ (US); Hy Si Bui, Piscataway, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/986,296

(22) Filed: Dec. 31, 2015

(65) Prior Publication Data

US 2017/0189311 A1    Jul. 6, 2017

(51) Int. Cl.
| | |
|---|---|
| *A61K 8/88* | (2006.01) |
| *A61Q 3/02* | (2006.01) |
| *A61K 8/81* | (2006.01) |
| *A61K 8/84* | (2006.01) |

(52) U.S. Cl.
CPC .............. *A61K 8/88* (2013.01); *A61K 8/8147* (2013.01); *A61K 8/84* (2013.01); *A61Q 3/02* (2013.01); *A61K 2800/594* (2013.01); *A61K 2800/95* (2013.01)

(58) Field of Classification Search
CPC ............ C08G 18/025; A61K 2800/594; A61K 2800/882; A61K 2800/884; A61K 8/8147; A61K 8/88; A61K 2800/48; A61K 2800/95; A61K 8/8141; A61K 8/8152; A61K 8/817; A61K 8/84; A61Q 3/02
See application file for complete search history.

(56) References Cited

U.S. PATENT DOCUMENTS

| | | | |
|---|---|---|---|
| 3,288,770 A | 11/1966 | Butler | |
| 3,412,019 A | 11/1968 | Hoover | |
| 3,628,544 A | 12/1971 | Kalopissis | |
| 4,772,462 A | 9/1988 | Boothe et al. | |
| 4,939,210 A | 7/1990 | Imashiro et al. | |
| 5,079,326 A | 1/1992 | Suzuki et al. | |
| 5,219,648 A | 6/1993 | Morimoto et al. | |
| 5,248,783 A | 9/1993 | OLenick | |
| 5,321,101 A | 6/1994 | Suzuki et al. | |
| 5,338,794 A | 8/1994 | Imashiro et al. | |
| 5,352,400 A * | 10/1994 | West ................ | C07C 267/00 528/48 |
| 5,360,933 A | 11/1994 | Imashiro et al. | |
| 5,373,080 A | 12/1994 | Imashiro et al. | |
| 5,637,769 A | 6/1997 | Imashiro et al. | |
| 5,700,935 A | 12/1997 | Takenishi et al. | |
| 5,728,432 A | 3/1998 | Imashiro et al. | |
| 5,739,371 A | 4/1998 | OLenick, Jr. | |
| 5,789,588 A | 8/1998 | Takenishi et al. | |
| 5,843,670 A | 12/1998 | Suzuki et al. | |
| 5,849,404 A | 12/1998 | Amano et al. | |
| 5,856,014 A | 1/1999 | Imashiro et al. | |
| 5,856,479 A | 1/1999 | Suzuki et al. | |
| 5,859,166 A | 1/1999 | Sasaki et al. | |
| 5,889,096 A | 3/1999 | Imashiro et al. | |
| 5,908,746 A | 6/1999 | Suzuki et al. | |
| 5,912,290 A | 6/1999 | Imashiro et al. | |
| 5,912,344 A | 6/1999 | Suzuki et al. | |
| 5,939,200 A | 8/1999 | Amano et al. | |
| 5,958,516 A | 9/1999 | Imashiro et al. | |
| 5,973,024 A | 10/1999 | Imashiro et al. | |
| 6,017,742 A | 1/2000 | Takenishi et al. | |
| 6,063,890 A * | 5/2000 | Tye ................... | C08G 59/4042 528/45 |
| 6,103,836 A | 8/2000 | Imashiro et al. | |
| 6,107,378 A | 8/2000 | Imashiro et al. | |
| 6,111,017 A | 8/2000 | Imashiro et al. | |

(Continued)

FOREIGN PATENT DOCUMENTS

| | | |
|---|---|---|
| CN | 104910635 A | 9/2015 |
| CN | 105813626 A | 7/2016 |

(Continued)

OTHER PUBLICATIONS

EPO Search Report, dated Mar. 15, 2017, 15 pages.
EPO Search Report, dated Mar. 10, 2017, 13 pages.
EPO Search Report, dated May 4, 2017, 20 pages.
EPO Search Report dated Mar. 20, 2017, 14 pages.
Milczarek, et al., Colloid Polym. Sci., 270, 1006-1115 (1992).
U.S. Appl. No. 14/986,019, filed Dec. 31, 2015, US 20170189301 A1, Siliu Tan et al.
U.S. Appl. No. 15/396,083, filed Dec. 30, 2016, US 20170189313-A1, Siliu Tan et al.
PCT/US2016/069536, Dec. 30, 2016, WO 2017/117543, Christopher M. MacNeill et al.
U.S. Appl. No. 14/986,370, filed Dec. 31, 2015, US 20170189304-A1, Andrea M. Elsen-Wahrer et al.
U.S. Appl. No. 14/986,385, filed Dec. 31, 2015, US 20170189307-A1, Aditi Gogineni et al.

(Continued)

Primary Examiner — Mark V Stevens
(74) Attorney, Agent, or Firm — McNees Wallace & Nurick LLC

(57) ABSTRACT

Compositions including polycarbodiimide together with latex compounds to enhance the quality of the keratinous substrates. The present invention relates to a cosmetic treatment and process for treating keratinous materials, in particular for nail polishes and other treatments, where, according to the process, the polycarbodiimide and latex actives may be applied in a nail treatment that is a single step or at least two sequential steps. The ratio of the latex compound to the polycarbodiimide compound is in the range from about 50:50 to about 95:5, and the composition comprises 10 to 100% of a combined amount of the polycarbodiimide compound and the latex compound, by weight, of the entire composition. It is in particular a nail treatment composition and process for providing one or more of improved adhesion, water resistance, and shine through crosslinking between the actives, thereby imparting long wear, good shine, nail protection, and easy removal.

36 Claims, No Drawings

(56) References Cited

U.S. PATENT DOCUMENTS

| | | | |
|---|---|---|---|
| 6,124,398 A | 9/2000 | Imashiro et al. |
| 6,126,860 A | 10/2000 | Imashiro et al. |
| 6,127,029 A | 10/2000 | Imashiro et al. |
| 6,127,477 A | 10/2000 | Imashiro et al. |
| 6,153,718 A | 11/2000 | Imashiro et al. |
| 6,166,466 A | 12/2000 | Amano et al. |
| 6,194,500 B1 | 2/2001 | Imashiro et al. |
| 6,300,425 B1 | 10/2001 | Amano et al. |
| 6,333,363 B1 | 12/2001 | Imashiro et al. |
| 6,420,035 B1 | 7/2002 | Amano et al. |
| 6,451,890 B1 | 9/2002 | Imashiro et al. |
| 6,461,755 B1 | 10/2002 | Saito et al. |
| 6,486,266 B2 | 11/2002 | Amano et al. |
| 6,642,380 B1 | 11/2003 | Kimura et al. |
| 6,656,682 B1 | 12/2003 | Suzuki et al. |
| 6,777,181 B2 | 8/2004 | Matsumoto |
| 6,803,139 B2 | 10/2004 | Saito et al. |
| 6,825,195 B2 | 11/2004 | Kimura |
| 6,846,860 B2 | 1/2005 | Takahashi et al. |
| 6,866,934 B2 | 3/2005 | Takahashi et al. |
| 6,979,703 B2 | 12/2005 | Takahashi et al. |
| 7,105,299 B2 | 9/2006 | Moriya et al. |
| 7,129,190 B2 | 10/2006 | Takahashi et al. |
| 7,135,293 B2 | 11/2006 | Kimura et al. |
| 7,238,518 B2 | 7/2007 | Matsubara et al. |
| 7,258,921 B2 | 8/2007 | Hashiba et al. |
| 7,273,902 B2 | 9/2007 | Takahashi et al. |
| 7,361,701 B2 | 4/2008 | Takahashi et al. |
| 7,368,493 B2 | 5/2008 | Takahshi et al. |
| 7,387,832 B2 | 6/2008 | Hashiba et al. |
| 7,425,062 B2 | 9/2008 | Bauer |
| 7,816,424 B2 | 10/2010 | Takahashi et al. |
| 8,604,154 B2 | 12/2013 | Takahashi et al. |
| 8,853,442 B2 | 10/2014 | Yanagisawa et al. |
| 8,969,471 B2 | 3/2015 | Hesselmans et al. |
| 9,056,302 B2 | 6/2015 | Jung et al. |
| 9,227,027 B2 | 1/2016 | Gurtner et al. |
| 2003/0220462 A1 * | 11/2003 | Porzio ............ C07C 267/00 528/44 |
| 2003/0228585 A1 | 12/2003 | Inoko et al. |
| 2004/0062737 A1 | 4/2004 | Nguyen et al. |
| 2006/0032175 A1 | 2/2006 | Chen et al. |
| 2006/0188577 A1 | 8/2006 | Kimura et al. |
| 2008/0020207 A1 | 1/2008 | Hashiba et al. |
| 2008/0124552 A1 | 5/2008 | Hashiba et al. |
| 2009/0274871 A1 | 11/2009 | Takahashi et al. |
| 2010/0160512 A1 | 6/2010 | Tsukamoto et al. |
| 2010/0222477 A1 | 9/2010 | Tsukamoto et al. |
| 2012/0022181 A1 * | 1/2012 | Xu ................ C09C 1/644 523/201 |
| 2012/0251925 A1 | 10/2012 | Sasaki |
| 2013/0144006 A1 | 6/2013 | Derksen et al. |
| 2014/0272419 A1 * | 9/2014 | Furar ............ C09D 175/04 428/413 |
| 2015/0004118 A1 | 1/2015 | Tan et al. |
| 2015/0166803 A1 * | 6/2015 | Jhaveri .......... C08F 265/06 427/385.5 |
| 2016/0060494 A1 * | 3/2016 | Patel ............ C08G 77/455 524/588 |
| 2016/0170091 A1 | 6/2016 | Li et al. |
| 2016/0262988 A1 | 9/2016 | Hayakawa et al. |

FOREIGN PATENT DOCUMENTS

| | | | |
|---|---|---|---|
| EP | 0259511 A1 * | 3/1988 | ............ C07C 275/06 |
| EP | 0436327 A1 | 7/1991 | |
| EP | 0219830 B1 | 4/1992 | |
| EP | 0713863 A1 | 5/1996 | |
| EP | 0789060 | 8/1997 | |
| EP | 0920852 A2 | 6/1999 | |
| EP | 1935275 A1 | 6/2008 | |
| EP | 3000821 A1 | 3/2016 | |
| FR | 2725620 | 4/1996 | |
| FR | 2782268 A1 | 2/2000 | |
| GB | 1163385 A | 9/1969 | |
| GB | 1186101 A | 4/1970 | |
| JP | 5124929 | 5/1993 | |
| JP | 2017500302 A | 1/2017 | |
| KR | 20130114468 A | 10/2013 | |
| KR | 101453216 B1 | 10/2014 | |
| KR | 101453217 B1 | 10/2014 | |
| KR | 101453218 B1 | 10/2014 | |
| KR | 101453219 B1 | 10/2014 | |
| KR | 101453220 B1 | 10/2014 | |
| KR | 20150066806 A | 6/2015 | |
| KR | 20150066829 A | 6/2015 | |
| KR | 101585343 B1 | 1/2016 | |
| KR | 101663053 B1 | 10/2016 | |
| KR | 101663055 B1 | 10/2016 | |
| KR | 101677006 B1 | 11/2016 | |
| RU | 2551276 C | 5/2015 | |
| WO | 9523579 A2 | 9/1995 | |
| WO | WO2009054312 | 3/2011 | |
| WO | WO 2014163917 A1 * | 10/2014 | |
| WO | 2015088126 A1 | 6/2015 | |
| WO | WO2015080671 A1 | 6/2015 | |
| WO | WO2015125117 A1 | 8/2015 | |
| WO | WO2015181365 A1 | 12/2015 | |
| WO | WO2015181366 A1 | 12/2015 | |
| WO | WO2015181369 A1 | 12/2015 | |
| WO | WO2016011319 A1 | 1/2016 | |
| WO | WO2016049456 A1 | 3/2016 | |
| WO | WO2016052834 A1 | 4/2016 | |
| WO | WO2016052931 A1 | 4/2016 | |
| WO | WO2017034367 A2 | 3/2017 | |

OTHER PUBLICATIONS

U.S. Appl. No. 15/396,119, filed Dec. 30, 2016, US 20170189308-A1, Aditi Gogineni et al.

U.S. Appl. No. 14/985,975, filed Dec. 31, 2015, US 20170189314-A1, Andrea M. Elsen-Wahrer et al.

U.S. Appl. No. 15/396,189, filed Dec. 30, 2016, US 20170189309-A1, Andrea M. Elsen-Wahrer et al.

PCT/US2016/069485, Dec. 30, 2016, WO 2017/117526, Andrea M. Elsen-Wahrer et al.

U.S. Appl. No. 14/986,047, filed Dec. 31, 2015, US 20170189302-A1, Aditi Gogineni et al.

PCT/US2016/069553, Dec. 30, 2016, WO 2017/117552, Aditi Gogineni et al.

U.S. Appl. No. 14/986,283, filed Dec. 31, 2015, US 20170189303-A1, Aditi Gogineni et al.

U.S. Appl. No. 14/986,114, filed Dec. 31, 2015, US 20170189319-A1, Aditi Gogineni et al.

PCT/US2016/069472, Dec. 30, 2016, WO 2017/117522, Aditi Gogineni et al.

U.S. Appl. No. 15/395,453, filed Dec. 30, 2016, US 20170189306-A1, Nghi Van Nguyen et al.

U.S. Appl. No. 15/395,484, filed Dec. 30, 2016, US 20170189312-A1, Nghi Van Nguyen et al.

U.S. Appl. No. 15/637,310, filed Jun. 29, 2017, Ronak Rughani et al.

U.S. Appl. No. 15/636,891, filed Jun. 29, 2017, Ronak Rughani et al.

U.S. Appl. No. 15/637,819, filed Jun. 29, 2017, Aditi Gogineni et al.

* cited by examiner

NAIL POLISH COMPOSITIONS

FIELD OF THE INVENTION

The present invention generally relates to a nail polish composition. More particularly, the present invention relates to keratinous treatment compositions having a polycarbodiimide compound, and a latex.

BACKGROUND OF THE INVENTION

Traditional nail polish products contain a large amount of cellulose based polymers such as nitrocellulose, primarily because cellulose based polymers provide good adhesion of the compositions to nails upon application. Although nitrocellulose is the preferred adhesive agent for use in conventional nail polish compositions and it constitutes the "gold standard" of adhesive agents in nail polish compositions, the traditional nail compositions containing nitrocellulose are generally known for poor long wear characteristics. The use of low levels of nitrocellulose tends to result in the coated films being easily damaged. On the other hand, the use of high levels of nitrocellulose results in the nail polishes being too hard and inflexible. Further, nitrocellulose does not impart high gloss.

In the past, proposed solutions to improve adhesion and gloss included incorporating into compositions containing nitrocellulose high levels of plasticizers and replacing nitrocellulose with other alternative materials. For instance, U.S. Pat. No. 6,939,551 relates to the use of nitrocellulose in the presence of butyl phthalimide isopropyl phthalimide, and U.S. Pat. No. 8,790,669 discloses the use of latex film formers instead of nitrocellulose.

Despite such attempts, there remains a need for nail compositions which adhere, are glossy and have long wear properties.

BRIEF SUMMARY OF THE INVENTION

The present invention relates to a water based nail polish composition containing at least one polycarbodiimide compound and at least one latex compound as film formers. Such nail compositions can be easily removed with less damage to nails and without sacrificing the long wear properties and complicating the application.

In an exemplary embodiment, the polycarbodiimide comprises of an oligomeric or polymeric structure that contains one or more carbodiimide functional groups, and the latex film former comprises a latex or pseudolatex. In exemplary embodiments, the latex compound comprises colloidal dispersions of polymer particles in an aqueous liquid phase, generally obtained by suspension or emulsion polymerization or copolymerization of monomers according to processes that are well known to those of ordinary skill in the art.

In an exemplary embodiment, a nail composition is provided that includes at least one primary film former comprising a latex compound and a polycarbodiimide compound. According to various embodiments, the ratio of the latex compound to the polycarbodiimide compound is in the range from about 50:50 to about 95:5, and the composition comprises 10 to 95% of a combined amount of the polycarbodiimide compound and the latex compound, by weight, of the entire composition. In some embodiments, the composition comprises one or more additives, including but not limited to, at least one solvent, at least one adhesive agent, and at least one secondary film former.

According to such embodiments, the ratios of the at least one latex to the at least one polycarbodiimide is in the range from about 50:50 to about 95:5, and more particularly from about 70:30 to about 90:10, and even more particularly about 80:20, including all ranges and subranges therebetween. In various embodiments, the combination of latex and polycarbodiimide constitute, as a percentage of the weight of the nail composition, from about 10% to 95%, and in some embodiments, from about 20% to about 75%, and in some particular embodiments, about 28% to 35%.

In some particular embodiments, a nail composition is provided wherein the ratio of the latex compound to the polycarbodiimide compound is in the range from about 70:30 to about 90:10. In certain embodiments, the ratio of the latex compound to the polycarbodiimide compound is about 80:20.

The present invention is also directed to a method for cosmetic treatment of keratinous tissues by applying the above-disclosed composition onto a surface of the keratinous tissue.

Other features and advantages of the present invention will be apparent from the following more detailed description of the exemplary embodiment which illustrates, by way of example, the principles of the invention.

DETAILED DESCRIPTION OF THE INVENTION

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"Active material" as used herein with respect to the percent amount of an ingredient or raw material, refers to 100% activity of the ingredient or raw material.

"Adhesion" as used herein, refers to chemical and/or physical bonding between a coating and a substrate. Good adhesion between nail polish and nail surface should translate to good wear properties on consumers.

"Adhesive agent" or "adhesive" means a polymer that improves chemical and/or physical bonding between a coating and a substrate. In this invention, the adhesive agent improves bonding between compositions and the nail surface or other compositions.

"Comprising" (and its grammatical variations) as used herein is used in the inclusive sense of "having" or "including" and not in the exclusive sense of "consisting only of."

"Film former", "film-forming polymer" or "film forming agent" or "co-film former" as used herein means a polymer or resin that is capable, by itself or in the presence of an auxiliary film-forming agent, of forming a macroscopically continuous film that adheres on the substrate to which it is applied, for example, after a solvent accompanying the film former has evaporated, absorbed into and/or dissipated on the substrate. In addition, as used herein, a non-film-forming polymer is meant to include a polymer which will not form a film at ambient temperature. For purposes of this disclosure, ambient temperature is taken as being below 40° C. such as in the range of 15° C. to 30° C.

"Free" or "devoid" of as it is used herein means that while it is preferred that no amount of the specific component be present in the composition, it is possible to have very small amounts of it in the compositions of the invention provided that these amounts do not materially affect at least one, in some embodiments most, of the advantageous properties of the compositions of the invention. Thus, for example, "free of solvents" means that non-aqueous solvents are, in some embodiments omitted (that is 0% by weight), but can be present in the composition at an amount of less than about 0.25% by weight, typically less than about 0.1% by weight, typically less than about 0.05% by weight, based on the total weight of the composition.

"Hardness" as used herein, means how resistant a material is to various kinds of permanent shape change when a force is applied. The force can be measured and quantified as described ahead in this application.

"High humidity," as defined herein, refers to atmospheric humidity above 40%.

"Homogeneous" means having the visual appearance of being substantially uniform throughout, i.e., visually appears as a single-phase emulsion and/or dispersion.

"Keratinous substrate," as used herein, includes, but is not limited to, skin, hair, and nails. "Keratinous substrate" as used herein also includes "keratinous tissue" or "keratinous fibers," which as defined herein, may be human keratinous fibers, and may be chosen from, for example, hair, such as hair on the human head, or hair comprising eyelashes or hair on the body.

"Nail composition" or "lacquer" or "nail polish" or "nail enamel" or "nail coating" or "nail film" refers to nail enamel usable as a basecoat, color coat, top coat, clear coat and protective coat applied on nails separately and/or as a combined application of the above.

"Nail treatment system" means multiple compositions applied on the surface of nails.

"Nails", "fingernail or "toenail" refers to a human keratinous substrate on a finger or toe which can be treated (decorated) with a single or multiple nail cosmetic compositions.

"Polymer or copolymer having a high acid value (number)" means polymer or copolymer which requires a high amount (in milligrams) of potassium hydroxide (KOH) to neutralize the acid that is present in one gram of a sample of the polymer (i.e., mg KOH/gram).

"Removal" or "Easy removal" means the composition may be substantially removed with water, acetone or other organic solvents not limited to butyl acetate, isopropyl alcohol, ethanol, ethyl acetate, methyl acetate, methyl ethyl ketone, and mixtures thereof.

"Shine" or "gloss" as used herein, refers to surface shininess. Gloss meters are commonly used in the nail polish art as well as in other areas of cosmetics, and measure the amount of light reflected from the surface or film of interest. The gloss may be quantified, for example, as a % reflectance at 20°.

"Shine enhancing agent" or "shine increasing agent" in accordance with the present invention means increasing shine or, as the case may be, mitigating or reducing any reduction in shine that may result from the use of corresponding amounts of non-shine enhancing materials.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Treat" (and its grammatical variations) as used herein refers to the application of the compositions of the present invention onto keratinous substrates such as keratinous fibers or hair or skin.

"Water free" or "free of water" herein means that water is in some embodiments omitted (that is 0% by weight), but can be present in the composition at an amount of less than about 0.25% by weight, typically less than about 0.1% by weight, typically less than about 0.05% by weight, based on the total weight of the composition.

"Water resistance" as used herein, means resistance of a material (substance) to the penetration of water, which may cause degradation of that material. The method implemented if assessment of this invention is further disclosed.

Referred to herein are trade names for materials including, but not limited to polymers and optional components. The inventors herein do not intend to be limited by materials described and referenced by a certain trade name. Equivalent materials (e.g., those obtained from a different source under a different name or catalog (reference) number) to those referenced by trade name may be substituted and utilized in the methods described and claimed herein.

All percentages and ratios are calculated by weight unless otherwise indicated. All percentages are calculated based on the total weight of a composition unless otherwise indicated. All component or composition levels are in reference to the active level of that component or composition, and are exclusive of impurities, for example, residual solvents or by-products, which may be present in commercially available sources.

It has been surprisingly and unexpectedly discovered by the inventors that the association polycarbodiimides with latexes, particularly carboxylic acid containing latex polymers, provides enhanced properties to keratinous substrates, in particular nails. The association is useful for cosmetic application to keratinous substrates, such as nails, whereby the combination of the latex polymers and polycarbodiimides react to each other and to the keratin substrate to enhance the properties, including but not limited to adhesion, chemical resistance, and water resistance etc. and deliver superior performance to the substrate. In some embodiments, a water-based nail composition according to the disclosure comprises at least one carboxylic acid functionalized latex polymer and at least one polycarbodiimide polymer. Each of the at least one polycarbodiimide and latex polymers can react and cross-link with the other on the nail surface at room temperature after drying and continue to crosslink over the course of five days. The nail enamel has good adhesion, shine, water resistance and hardness compared to other water based nail enamels. The nail enamel can also be easily removed, which is advantageous for latex based nail enamels due to their inability to dissolve quickly with solvent based remover.

Nail polish compositions traditionally contain nitrocellulose, as the primary film former, along with organic solvents that can impart a harsh smell. In recent years, consumers have become more concerned with the side effects of these solvents while applying and removing traditional nitrocellulose-based nail enamel. Most latex film formers that show good wear properties suffer from relatively low shine and difficult removal properties. The removal of latex film formers consist of either soaking in water or acetone for up to 10 minutes. Prolonged exposure to solvents during removal can cause damage to the nails by making them dry and brittle. Consumers are looking for a water based nail enamel that exhibits long wear properties with a fast, safe removal and no nail damage. By reacting polycarbodiimides with latex film formers, enhanced properties, including water resistance, adhesion, and chemical resistance can be provided while obtaining an easy removal of the nail polish with no nail damage.

According to the disclosure, in various embodiments a low VOC water-based nail enamel is provided that does not contain nitrocellulose or harsh organic solvents, the nail enamel comprising polycarbodiimide and waterborne latex as the primary film formers, to provide good adhesion and shine. Polycarbodiimides are multifunctional polymers that contain carbodiimide (N=C=N) groups along their polymer backbone that can react with carboxylic acid groups (—COOH) on waterborne latex resins at room temperature to form a multidimensional cross-linked network film that can increase water resistance, hardness and adhesion compared to waterborne latex resins alone.

A carbodiimide group is a linear triatomic moiety generally depicted by Formula (I):

(I)

At least one of the nitrogens is linked to or incorporated into a backbone or other bridging group to result in a molecule having at least two carbodiimide groups.

Polycarbodiimides

In one embodiment, the polycarbodiimides comprising of at least two carbodiimide units, as described above, can be represented by Formula (II):

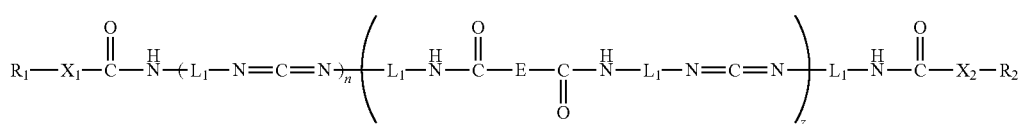

(II)

wherein $X_1$ and $X_2$ each independently represent O, S or NH. $R_1$ and $R_2$ are selected from a hydrocarbon group containing one or more catenary or non-catenary heteroatoms, such as nitrogen, sulfur and oxygen, and linear or branched and cyclic or acyclic groups which can be ionic or non-ionic segments, or a partially or fully fluorinated hydrocarbon group that may contain one or more catenary or non-catenary hetero-atoms; n and z are, each independently, an integer of 0 to 20; $L_1$ (Linker of carbodiimide groups) is selected from a $C_1$ to $C_{18}$ divalent aliphatic hydrocarbon group, a $C_3$ to $C_{13}$ divalent alicyclic hydrocarbon group, a $C_6$ to $C_{14}$ divalent aromatic hydrocarbon group, and a $C_3$ to $C_{12}$ divalent heterocyclic group; wherein a plurality of $L_1$s may be identical to or different from one another, and wherein in another embodiment, $L_1$ of formula (II) is selected from a $C_1$ to $C_{18}$ divalent aliphatic hydrocarbon group, a $C_3$ to $C_{13}$ divalent alicyclic hydrocarbon group, a $C_6$ to $C_{14}$ divalent aromatic hydrocarbon group that is not chosen from m-tetramethylxylylene, and a $C_3$ to $C_{12}$ divalent heterocyclic group; wherein a plurality of $L_1$s may be identical to or different from one another;

wherein E is a radical selected from the following formulas:

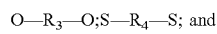

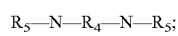

wherein $R_3$ and $R_4$ are each independently hydrocarbon radicals that may contain halogen atoms or one or more catenary (i.e.; in chain, bonded only to carbon) or non-catenary hetero atoms, including an aromatic, cycloaliphatic, aryl and alkyl radical (linear or branched) and $R_5$ is hydrogen, or a hydrocarbon radical which can contain halogen atoms or one or more catenary (i.e.; in chain, bonded only to carbon) or non-catenary hetero atoms.

Examples of R1 and R2 can be methyl glycolate, methyl lactate, polypropylene glycol, polyethylene glycol monomethyl ether, dialkylamino alcohol.

Examples of L1 can be the diradical of tolylene, hexamethylene, hydrogenated xylylene, xylylene, 2,2,4-trimethylhexamethylene, 1,12-dodecane, norbornane, 2,4-bis-(8-octyl)-1,3-dioctylcyclobutane, 4,4'-dicyclohexylmethane, tetramethylxylylene, isophorone, 1,5-naphthylene, 4,4' diphenylmethane, 4,4' diphenyldimethylmethane, phenylene.

Polycarbodiimides may include polymers with a plurality of carbodiimide groups appended to the polymer backbone. For example, U.S. Pat. No. 5,352,400 (the disclosure of which is incorporated by reference herein for all purposes as if fully set forth) discloses polymers and co-polymers derived from alpha-methylstyryl-isocyanates. Such a polymer is illustrated in Formula (III).

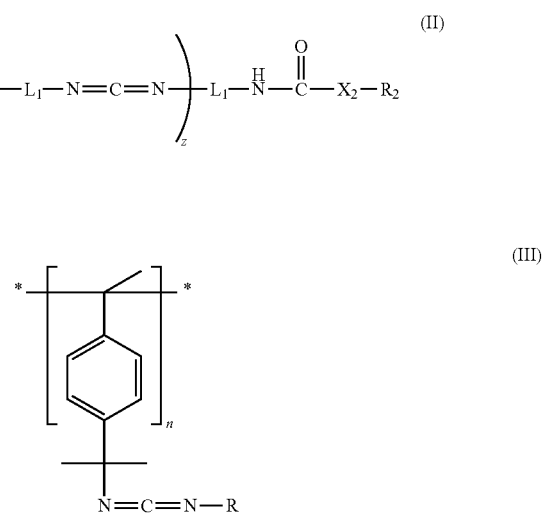

(III)

wherein R is an alkyl, cycloalkyl or aryl group (in some particular embodiments having from 1 to 24 carbon atoms).

In another embodiment, polycarbodiimides, according to the present disclosure, include polycarbodiimides having branched structures, like that shown in Formula (IV), and as described in Chapter 8 of Technology for Waterborne Coatings, E. J. Glass Ed., ACS Symposium 663, 1997; The Application of Carbodiimide Chemistry to Coating, by J. W. Taylor and D. R. Bassett (the disclosure of which is incorporated by reference herein for all purposes as if fully set forth).

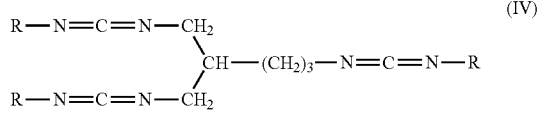

wherein R is an alkyl, cycloalkyl or aryl group (in some particular embodiments having from 1 to 24 carbon atoms).

In one embodiment, the compositions of the present disclosure does not employ a polycarbodiimide having a linker $L_1$ chosen from m-tetramethylxylylene.

Suitable polycarbodiimide compounds include, but are not limited to, those commercially sold by the suppliers Nisshinbo, Picassian, and 3M. Particularly suitable polycarbodiimide compounds include, but are not limited to, those known by the name under the CARBODILITE series, V-02, V02-L2, SV-02, E-02, V-10, SW-12G, E-03A, commercially sold by Nisshinbo.

In some embodiments, the polycarbodiimide of the present disclosure is selected from compounds of formula (II) wherein L1 (Linker of carbodiimide groups) represents a C1 to C18 divalent aliphatic hydrocarbon group, a C3 to C13 divalent alicyclic hydrocarbon group, a C3 to C12 divalent heterocyclic group, or a C6 to C14 divalent aromatic hydrocarbon group;

wherein a plurality of L1s may be identical to or different from one another.

In other embodiments, the polycarbodiimide of the present disclosure is selected from compounds of formula (II) wherein L1 is not chosen from m-tetramethylxylylene.

The polycarbodiimide is typically present in the composition of the present disclosure in an amount of from about 1% to about 30%, by weight, in some embodiments from about 5% to about 20%, by weight, and in some embodiments from about 6% to about 15%, by weight, including all ranges and subranges therebetween, based on the total weight of the composition.

Thus, in various embodiments, the amount of the polycarbodiimide in the composition of the present disclosure is about 0.25%, 0.5%, 0.55%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10% 12%, 14%, 15%, 16%, 18%, 20%, and 30%, by weight, including all ranges and subranges therebetween, based on the total weight of the composition.

Latex Polymers

According to various exemplary embodiments, the compositions of the present invention can further comprise one or more latex polymers (also referred to as "latex polymers" in this application) can be chosen from carboxyl functional acrylate latex polymers, carboxyl functional polyurethane latex polymers, carboxyl functional silicone latex polymers, carboxyl functional non-acrylate latex polymers and mixtures thereof.

In various embodiments, the latex polymers of the present invention can be film-forming latex polymers or non film-forming latex polymers.

In at least certain embodiments of the disclosure, the latex polymers are provided in the form of aqueous dispersions prior to formulating the compositions of the disclosure. In various embodiments, the aqueous dispersions may be obtained through an emulsion polymerization of monomers wherein the resulting latex polymers have a particle size lower than about 1 micron. In at least one exemplary embodiment, a dispersion prepared by the polymerization in water of one or more monomers having a polymerizable double bond may be chosen. In another exemplary embodiment, the aqueous dispersions obtained through an emulsion polymerization may be spray-dried.

In other embodiments, the latex polymers are produced from condensation reactions between monomers and subsequently dispersed in an aqueous medium.

Thus, the latex polymers may, in various exemplary embodiments, exist as dispersed polymer particles in a dispersion medium, such as an aqueous dispersion medium. The latex polymers may, in various embodiments, each be dispersed in independent dispersion media or dispersed together in the same dispersion medium.

The dispersion medium comprises at least one solvent chosen from water. The dispersion medium may further comprise at least one solvent chosen from cosmetically acceptable organic solvents such as those described above.

In embodiments according to the disclosure, the latex polymer particles are not soluble in the solvent of the dispersion medium, i.e. are not water soluble and/or are not soluble in the at least one cosmetically acceptable organic solvent. Accordingly, the latex polymers retain their particulate form in the solvent or solvents chosen.

In at least certain exemplary embodiments, latex polymer particles according to the disclosure may have an average diameter ranging up to about 1000 nm, such as from about 50 nm to about 800 nm, or from about 100 nm to about 500 nm. Such particle sizes may be measured with a laser granulometer (e.g. Brookhaven BI90).

In various embodiments, the latex polymers may, independently, be neutralized, partially neutralized, or unneutralized. In exemplary embodiments where the latex polymers are neutralized or partially neutralized, the particle size may be, for example, greater than about 800 nm. In at least certain embodiments, the particulate form of the latex polymers is retained in the dispersion medium.

In further embodiments, the latex polymers may be chosen from uncharged and charged latex polymers. Thus, the latex polymers may, according to various exemplary embodiments, be chosen from nonionic latex polymers, cationic latex polymers, anionic latex polymers and amphoteric latex polymers.

By way of non-limiting example only, the latex polymers may be chosen from carboxyl functional acrylate latex polymers, such as those resulting from the homopolymerization or copolymerization of ethylenically unsaturated monomers chosen from vinyl monomers, (meth)acrylic monomers, (meth)acrylamide monomers, mono- and dicarboxylic unsaturated acids, esters of (meth)acrylic monomers, and amides of (meth)acrylic monomers The term "(meth)acryl" and variations thereof, as used herein, means acryl or methacryl.

The (meth)acrylic monomers may be chosen from, for example, acrylic acid, methacrylic acid, citraconic acid, itaconic acid, maleic acid, fumaric acid, crotonic acid, and maleic anhydride. The esters of (meth)acrylic monomers may be, by way of non-limiting example, C1-C8 alkyl (meth)acrylates such as methyl (meth)acrylate, ethyl (meth)acrylate, propyl (meth)acrylate, isopropyl (meth)acrylate, butyl (meth)acrylate, tert-butyl (meth)acrylate, pentyl(meth) acrylate, isopentyl (meth)acrylate, neopentyl (meth)acrylate, hexyl (meth)acrylate, isohexyl (meth)acrylate, 2-ethylhexyl (meth)acrylate, cyclohexyl (meth)acrylate, isohexyl (meth)acrylate, heptyl (meth)acrylate, isoheptyl (meth)acrylate, octyl (meth)acrylate, isooctyl (meth)acrylate, allyl (meth)acrylate, and combinations thereof. The amides of (meth)acrylic monomers can, for example, be made of (meth)acrylamides, and especially N-alkyl (meth)acrylamides, in particular N—(C1-C12) alkyl (meth)acrylates such as N-ethyl (meth)acrylamide, N-t-butyl (meth)acrylamide, N-t-octyl (meth)acrylamide, N-methylol (meth)acrylamide and N-diacetone (meth)acrylamide, and any combination thereof.

The vinyl monomers can include, but are not limited to, vinyl cyanide compounds such as acrylonitrile and methacrylonitrile; vinyl esters such as vinyl formate, vinyl acetate, vinyl propionate, vinyl neodecanoate, vinyl pivalate, vinyl benzoate and vinyl t-butyl benzoate, triallyl cyanurate; vinyl halides such as vinyl chloride and vinylidene chloride; aromatic mono- or divinyl compounds such as styrene, α-methylstyrene, chlorostyrene, alkylstyrene, divinylbenzene and diallyl phthalate, as well as para-styrensulfonic, vinylsulfonic, 2-(meth)acryloyloxyethylsulfonic, 2-(meth)acrylamido-2-methylpropylsulfonic acids, and mixtures thereof.

The list of monomers given is not limiting, and it should be understood that it is possible to use any monomer known to those skilled in the art which includes acrylic and/or vinyl monomers (including monomers modified with a silicone chain).

In at least certain, non-limiting exemplary embodiments carboxyl functional acrylate latex polymers may be chosen from aqueous dispersions of Methacrylic Acid/Ethyl Acrylate copolymer (INCI: Acrylates Copolymer, such as Luviflex® SOFT by BASF), PEG/PPG-23/6 Dimethicone Citraconate/C10-30 Alkyl PEG-25 Methacrylate/Acrylic Acid/Methacrylic Acid/Ethyl Acrylate/Trimethylolpropane PEG-15 Triacrylate copolymer (INCI: Polyacrylate-2 Crosspolymer, such as Fixate Superhold™ by Lubrizol), Styrene/Acrylic copolymer (such as Acudyne Shine by Dow Chemical), Ethylhexyl Acrylate/Methyl Methacrylate/Butyl Acrylate/Acrylic Acid/Methacrylic Acid copolymer (INCI: Acrylates/Ethylhexyl Acrylate Copolymer, such as Daitosol 5000SJ, Daito Kasei Kogyo), Acrylic/Acrylates Copolymer (INCI name: Acrylates Copolymer, such as Daitosol 5000AD, Daito Kasei Kogyo), Acrylates Copolymers, such as those known under the tradenameDermacryl AQF (Akzo Nobel), under the tradename LUVIMER® MAE (BASF), or under the tradename BALANCE CR (AKZO NOBEL), Acrylates/Hydroxyesters Acrylates Copolymer, known under the tradename ACUDYNE 180 POLYMER (Dow Chemical), Styrene/Acrylates Copolymer, known under the tradename Acudyne Bold from Dow Chemical, Styrene/Acrylates/Ammonium Methacrylate Copolymer, known under the tradename SYNTRAN PC5620 CG from Interpolymer, and mixtures thereof.

In yet further exemplary and non-limiting embodiments, the latex polymers may be chosen from carboxyl functional polyurethane latex polymers, such as aqueous polyurethane dispersions. These polyurethanes are conventionally formed by the reaction of prepolymer (i) with a coreactant (ii) to produce a carboxyl terminated or pendant polyurethane polymer. The prepolymer (i) may have the structure according to the formula (I'):

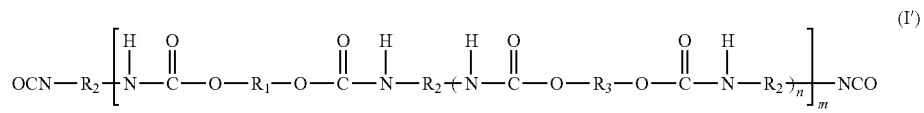

wherein R1 is chosen from bivalent radicals of a dihydroxyl functional compound, R2 is chosen from hydrocarbon radicals of an aliphatic or cycloaliphatic polyisocyanate, and R3 is chosen from radicals of a low molecular weight diol, optionally substituted with ionic groups or potential ionic groups, n ranges from about 0 to about 5, and m is greater than about 1.

Suitable dihydroxyl compounds for providing the bivalent radical R1 include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, and polyhydroxy polycarbonates may be chosen. Mixtures of such compounds are also within the scope of the disclosure.

Optional polyisocyanates for providing the hydrocarbon-based radical R2 include, for example, organic diisocyanates having a molecular weight ranging from about 100 to about 1500, such as about 112 to about 1000, or about 140 to about 400.

Optional diisocyanates are those chosen from the general formula R2(NCO)2, in which R2 represents a divalent aliphatic hydrocarbon group comprising from about 4 to 18 carbon atoms, a divalent cycloaliphatic hydrocarbon group comprising from about 5 to 15 carbon atoms, a divalent aromatic hydrocarbon group comprising from about 7 to 15 carbon atoms, or a divalent aromatic hydrocarbon group comprising from about 6 to 15 carbon atoms.

The use of diols, for example low molecular weight diols, R3, may in at least certain embodiments allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain exemplary embodiments, the compounds contain only aliphatic groups. The diols that may be chosen may optionally have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis(4-hydroxyphenyl)propane), hydrogenated bisphenol A (2,2-bis(4-hydroxycyclohexyl)-propane), and mixtures thereof. For example, R3 may be derived from neopentyl glycol.

Optionally, the low molecular weight diols may contain ionic or potentially ionic groups. Suitable low molecular weight diols containing ionic or potentially ionic groups may be chosen from those disclosed in U.S. Pat. No.

3,412,054. In various embodiments, compounds may be chosen from dimethylolbutanoic acid (DMBA), dimethylolpropionic acid (DMPA), and carboxyl-containing caprolactone polyester diol. If low molecular weight diols containing ionic or potentially ionic groups are chosen, they may, for example, be used in an amount such that less than about 0.30 meq of —COOH is present per gram of polyurethane in the polyurethane dispersion. In at least certain exemplary and non-limiting embodiments, the low molecular weight diols containing ionic or potentially ionic groups are not used.

Coreactants (ii) are compounds containing functional groups such as hydroxy or amine groups, preferably primary amine, adapted to react with isocyanate groups in preference to the carboxyl group according to the formula (II'):

$$X—R4-X \quad X=OH, NH2, \tag{II'}$$

wherein $R_4$ represents a divalent aliphatic or cycloaliphatic or aromatic hydrocarbon group, optionally substituted with ionic groups or potentially ionic groups. In various embodiments, compounds may optionally be chosen from alkylene diamines, such as hydrazine, ethylenediamine, propylenediamine, 1,4-butylenediamine and piperazine; In various embodiments, compounds may optionally be chosen from alkylene diols, such as ethylene glycol, 1,4-butanediol (1,4-BDO or BDO), 1,6-hexanediol.

As used herein, ionic or potentially ionic groups may include groups comprising ternary or quaternary ammonium groups, groups convertible into such groups, carboxyl groups, carboxylate groups, sulphonic acid groups, and sulphonate groups. At least partial conversion of the groups convertible into salt groups of the type mentioned may take place before or during the mixing with water. Special compounds may be chosen from dimethylolbutanoic acid (DMBA), dimethylolpropionic acid (DMPA), or carboxyl functional polyester comprising excess equivalents of dicarboxylic acid reacted with lesser equivalents of glycol or carboxyl-containing caprolactone polyester diol.

R1, R2, R3, R4 can have at least one carboxyl group independently.

By way of non-limiting example, such latexes include, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as Luviset® P.U.R, BASF), a copolymer of hexylene glycol, neopentyl glycol, adipic acid, saturated methylene diphenyldiisocyanate and dimethylolpropanoic acid monomers (INCI name: polyurethane 2), a copolymer of PPG-17, PPG-34, isophorone diisocyanate and dimethylolpropanoic acid monomers (INCI name: polyurethane 4), a copolymer of isophthalic acid, adipic acid, hexylene glycol, neopentyl glycol, dimethylolpropanoic acid, isophorone diisocyanate and bis-ethylaminoisobutyl-dimethicone monomers (INCI name: polyurethane 6), Isophorone diisocyanate, cyclohexanedimethanol, dimethylol butanoic acid, polyalkylene glycol and N-methyl diethanolamine copolymer (INCI name: polyurethane 10), Trimethylolpropane, neopentyl glycol, dimethylol propionic acid, polytetramethylene ether glycol and isocyanato methylethylbenzene copolymer (INCI name: polyurethane 12), Isophorone diisocyanate, dimethylol propionic acid, and 4,4'-isopropylidenediphenol reacted with propylene oxide, ethylene oxide and PEG/PPG-17/3 copolymer (INCI name: polyurethane 14), Isophorone diisocyanate, adipic acid, triethylene glycol and dimethylolpropionic acid copolymer (INCI name: polyurethane 15), 2-Methyl-2,4-pentanediol, polymer with 2,2-dimethyl-1,3-propanediol, hexanedioic acid, methylenedicyclohexanediisocyanate and 2,2-di(hydroxymethyl)propanoic acid, hydrolysed, tris(2-hydroxyethyl)amine salts, reaction products with 1,2-ethanediamine (INCI name: polyurethane 17), Polyurethane-27 is a complex polymer that is formed by the reaction of Polyperfluoroethoxymethoxy Difluorohydroxyethyl Ether and isophorone diisocyanate (IPDI) to form a prepolymer. The prepolymer is further reacted with the triethylamine salt of 3-hydroxy-2-(hydroxymethyl)-2-methyl-1-propionic acid (INCI name: polyurethane 27), a complex polymer formed by reacting dimethylolpropionic acid and a polyester composed of Adipic Acid, Hexylene Glycol, Neopentyl Glycol with methylene dicyclohexyldiisocyanate (SMDI) to form a prepolymer. The prepolymer is neutralized with triethylamine and then chain-extended with hydrazine (INCI name: polyurethane 33).

The latex polymers of the present disclosure may also be chosen from silicone polymers having at least one carboxylic acid group (Carboxysilicone Polymers)

Silicone Polymers Having At Least One Carboxylic Acid Group (Carboxysilicone Polymers).

The silicone polymers having at least one carboxylic acid group, referred herein as carboxysilicone polymers, according to the present disclosure, may be an organopolysiloxane comprising:

(A) a compound having the following formula:

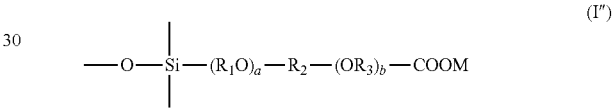

wherein $R_1$ and $R_3$ independently denote a linear or branched alkylene radical containing from 2 to 20 carbon atoms and $R_2$ denotes a linear or branched alkylene radical containing from 1 to 50 carbon atoms which can comprise a hydroxyl group, a represents 0 or 1, b is a number ranging from 0 to 200 and M denotes hydrogen, an alkali metal or alkaline-earth metal, NH4 or a quaternary ammonium group, such as a mono-, di-, tri- or tetra(C1-C4 alkylammonium) group, $R_1$ and $R_3$ can denote, for example, ethylene, propylene or butylene, or (B) a group comprising at least one pyrrolidone carboxylic acid unit having the following formula:

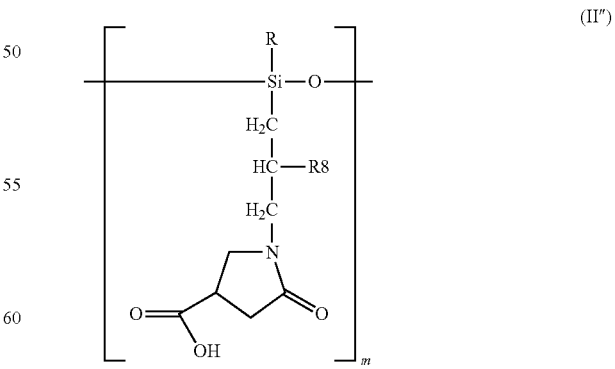

in which R is selected from methyl or phenyl; R8 is hydrogen or methyl, m is an integer from 1 to 1000, or (C) a group comprising at least one polyvinyl acid/ester unit (C) resulting from the polymerization of Divinyl- PDMS, Crotonic Acid, Vinylacetate, and Vinyl Isoalkylester, and combinations of (A), (B) and (C).

Suitable carboxysilicone polymers include, for example, a silicone polymer comprising at least one carboxylic acid group chosen from organopolysiloxanes of formula:

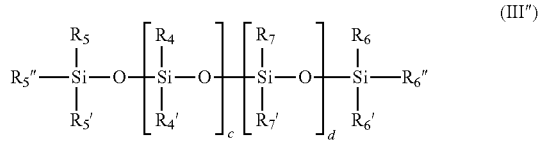

(III″)

wherein the radicals R4, R4' are identical to or different from each other and are chosen from a linear or branched C1-C22 alkyl radical, a C1-C22 alkoxy radical and a phenyl radical, the radicals R5, R5', R5″, R6, R6', R6″, R7, and R7' are identical to or different from each other and are chosen from a linear or branched C1-C22 alkyl radical, a C1-C22 alkoxy radical, a phenyl radical, a radical —(R1O)a-R2-(OR3)b-COOM, a radical containing pyrrolidone carboxylic acid, a radical of polyvinyl acid/ester; and wherein at least one of the radicals R5, R6 and R7 is a radical chosen from a radical —(R1O)a-R2-(OR3)b-COOM, a radical containing pyrrolidone carboxylic acid, a radical of polyvinyl acid/ester;

wherein R1, R2, R3, a, b and M have the same meaning as described in Unit (A) above;

wherein c and d are integers from 0 to 1000, the sum c+d in some particular embodiments ranging from 1 to 1000 or from 2 to 1000.

Among the carboxysilicone polymers of formula (III″) that comprise at least one unit (I″), which in some particular embodiments are the compounds of formula below:

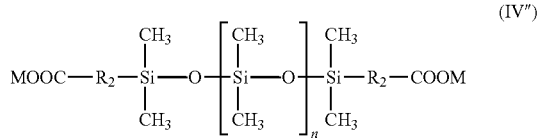

(IV″)

wherein R2, and M have the same meaning as described in Unit (A) above, n is an integer from 1 to 1000. Examples are: dual-end carboxy silicones X-22-162C from Shin Etsu and Silform INX (INCI name: Bis-Carboxydecyl Dimethicone) from Momentive.

Other exemplary embodiments organopolysiloxanes of formula (III″) are the ones of formula:

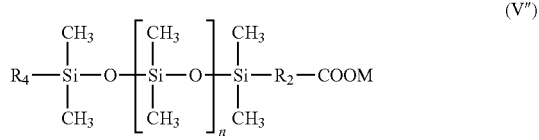

(V″)

in which R2, R4, n, and M having the same meaning as in Unit (A) above. An example is a single-end carboxy silicone X-22-3710 from Shin Etsu.

Other exemplary embodiments organopolysiloxanes of formula (III″) are the ones of formula:

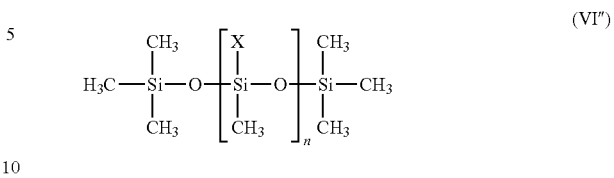

(VI″)

wherein X is a radical —(R1O)a-R2-(OR3)b-COOM wherein R1, R2, R3, a, b and M have the same meaning as described in Unit (A) above.

Even more particularly, the compounds of formula (VI′) in which a and b are equal to 0 and R2 is a linear or branched C2-C12 alkylene group such as (CH2)9, (CH2)10 or —CH(CH3)- are exemplary embodiments. An example is a side-chain carboxy silicone X-22-3701E from Shin Etsu.

Among the organopolysiloxanes of formula (III″) that contain unit (B), exemplary embodiments include the compounds of formula below:

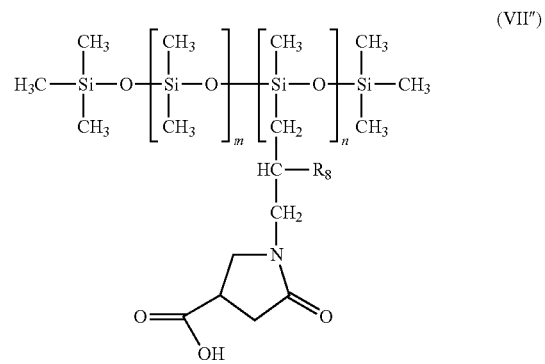

(VII″)

wherein R8, m, are defined as in Unit (B) above and n is an interger from 1 to 1000. An example is Grandsil PCA such as in Grandsil SiW-PCA-10 (INCI name: Dimethicone (and) PCA Dimethicone (and) Butylene Glycol (and) Decyl Glucoside from Grant Industries.

Among the organopolysiloxanes of formula (III″) that contain polyvinyl acid/ester Unit (C), exemplary embodiments are crosslinked anionic copolymers comprised of organic polymer blocks and silicone blocks, resulting in a multiblock polymer structure. In particular, the silicone-organic polymer compound of the present invention may be chosen from crosslinked anionic copolymers comprising at least one crosslinked polysiloxane structural unit. An example of such a branched multi-block carboxysilicone polymer is Belsil® P1101 (may also be known under the tradename Belsil® P1101) (INCI name: Crotonic Acid/Vinyl C8-12 Isoalkyl Esters/VA/Bis-Vinyldimethicone Crosspolymer, also known by the technical name of Crotonic Acid/Vinyl C8-12 Isoalkyl Esters/VA/divinyldimethicone Crosspolymer) from Wacker Chemie AG.

Additional suitable carboxysilicone polymers are described, for example, in patent applications WO 95/23579 and EP-A-0,219,830, which are hereby incorporated by reference in their entirety.

Compounds corresponding to formula (VI″) above are sold, for example, under the name HUILE M 642 by the company Wacker, under the names SLM 23 000/1 and SLM 23 000/2 by the company Wacker, under the name 176-12057 by the company General Electric, under the name FZ 3703 by the company OSI and under the name BY 16 880 by the company Toray Silicone.

Other non-limiting examples of carboxysilicone polymers are silicone carboxylate containing polymers (silicone carboxylates).

Suitable silicone carboxylates may be chosen from water soluble silicone compounds comprising at least one carboxylic acid group, oil soluble silicone compounds comprising at least one carboxylic acid group, water-dispersible silicone compounds comprising at least one carboxylic acid group, and silicone compounds comprising at least one carboxylic acid group which are soluble in organic solvents. In one embodiment, the silicone carboxylate further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups and propylene oxide groups.

The at least one carboxylic acid group may be chosen from terminal carboxylic acid groups and pendant carboxylic acid groups. Further, the at least one carboxylic acid may be chosen from carboxylic acid groups in free acid form, i.e., —COOH, and carboxylic acid groups in salt form, i.e., —COOM, wherein M may be chosen from inorganic cations, such as, for example, potassium cations and sodium cations, and organic cations.

In one embodiment, the silicone carboxylate is a compound of formula:

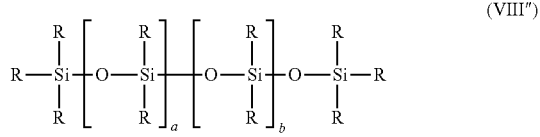

(VIII″)

wherein a is an integer ranging from 1 to 100; b is an integer ranging from 0 to 500; and R, which may be identical or different, are each chosen from optionally substituted hydrocarbon groups comprising from 1 to 9 carbon atoms, optionally substituted phenyl groups, and groups of the following formula:

—(CH$_2$)$_3$—O-(EO)$_c$—(PO)$_d$-(EO)$_e$—C(O)—R'—C(O)—OH   (IX″)

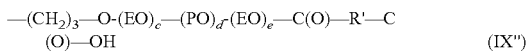

wherein c, d, and e, which may be identical or different, are each integers ranging from 0 to 20; EO is an ethylene oxide group; PO is a propylene oxide group; and R' is chosen from optionally substituted divalent hydrocarbons, such as alkylene groups and alkenylene groups comprising from 2 to 22 carbon atoms, and optionally substituted divalent aromatic groups, such as groups of the following formula (X″):

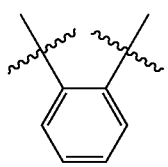

(X″)

and groups of the following formula (XI″):

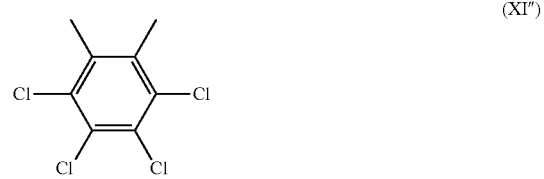

(XI″)

with the proviso that at least one of the R groups is chosen from groups of formula (VIII″) and with the further proviso that when only one of the R groups is chosen from groups of formula (VII″), the other R groups are not all methyl groups.

Non-limiting examples of silicone carboxylates include those commercially available from Noveon under the name Ultrasil® CA-1 Silicone (Dimethicone PEG-7 Phthalate) and Ultrasil® CA-2 Silicone (Dimethicone PEG-7 Succinate), both of which correspond to formula (XII″) below. Thus, in one embodiment, the at least one silicone carboxylate is chosen from a compound of formula below and salts thereof:

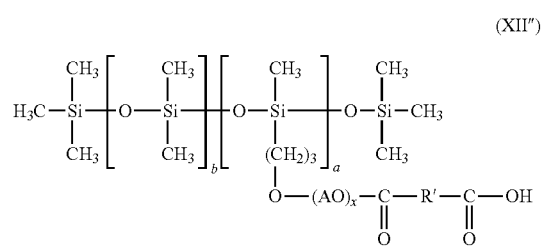

(XII″)

wherein a is an integer ranging from 1 to 100, b is an integer ranging from 0 to 500, AO is chosen from groups of the following formula (XIII″):

-(EO)c-(PO)d-(EO)e-   (XIII″)

wherein c, d, and e, which may be identical or different, are each integers ranging from 0 to 20; EO is an ethylene oxide group; PO is a propylene oxide group; x is an integer ranging from 0 to 60; R' is chosen from optionally substituted divalent hydrocarbons, such as alkylene groups and alkenylene groups comprising from 2 to 22 carbon atoms, and optionally substituted divalent aromatic groups, such as groups of the following formula (XIV″):

(XIV″)

and groups of formula (XV"):

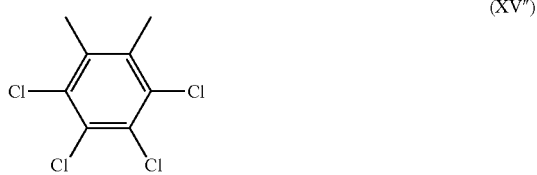

(XV")

Non-limiting examples of silicone carboxylates include those described in U.S. Pat. Nos. 5,248,783 and 5,739,371, the disclosures of which are incorporated herein by reference, and which are silicone compounds of formula (VIII").

In some particular examples according to the disclosure, latexes are formed and selected from monomers, in particular from styrene, butadiene, acrylonitrile, chloroprene, vinyl acetate, urethanes, isoprene, isobutylene, and acrylic or methacrylic acid, maleic acid, crotonic acid or itaconic acid or esters or amides thereof. Latex polymers particles comprise at least one acrylic acid-based or (meth)acrylic acid-based, monomer. Representative examples of suitable commercially available latexes include acrylic copolymer dispersions such as Euperlan PCO, Balance CR, Neocryl A45, Daitosol 3000 SLPN and Daitosol 3000 VP3.

The latex is typically present in the composition of the present disclosure in an amount of from about 5% to about 95%, by weight, in some embodiments from about 50% to about 95%, by weight, and in some embodiments from about 60% to about 80%, by weight, including all ranges and subranges therebetween, based on the total weight of the composition.

Thus, in various embodiments, the amount of the latex in the composition of the present disclosure is about 5%, 5.5%, 6%, 6.5%, 7%, 7.5%, 8%, 8.5%, 9%, 9.5%, 10% 12%, 14%, 15%, 16%, 18%, 20%, 30%. 40%, 50%, 60%, 70%, 80%, 90% and 95%, by weight, including all ranges and subranges therebetween, based on the total weight of the composition.

Nail composition comprising polycarbodiimide and latex film formers

In accordance with the present invention, nail compositions comprising film formers comprising a combination of at least one latex and at least one polycarbodiimide, the latex and polycarbodiimide selected from the various alternate embodiments as described herein above, are provided. According to such embodiments, the ratios of the at least one latex to the at least one polycarbodiimide is in the range from about 50:50 to about 95:5, and more particularly from about 70:30 to about 90:10, and even more particularly about 80:20, including all ranges and subranges therebetween. In various embodiments, the combination of latex and polycarbodiimide constitute, as a percentage of the weight of the nail composition, from about 10% to 100%, and in some embodiments, from about 40% to about 95%, and in some particular embodiments, about 60% to \95%.

Thus, in various embodiments, the amount of the combination of latex and polycarbodiimide in the composition of the present disclosure is about 10% 30%, 40%, 50%, 60%, 65%, 70%, 75% 80%, 85%, 90%, 95% and 100%, by weight, including all ranges and subranges therebetween, based on the total weight of the composition.

In accordance with the present invention, the nail compositions can be a base coat, a color coat or a top coat. However, it should be understood that each coat in the nail composition, itself, can comprise one or more layers. Thus, for example, the at least one color coat can comprise one or more color coat layers; the at least top coat can comprise one or more top coat layers; the at least one base coat can comprise one or more base coat layers. In various embodiments, each basecoat, color coat and topcoat compositions contain three or fewer layers of compositions, in some embodiments two or fewer layers of compositions, and in some further embodiments a single layer of compositions.

During application of the nail composition, the base coat is typically applied directly to the nail, the color coat is typically applied either directly to the nail or to a base coat, and the top coat is typically applied to a color coat.

The nail compositions of the present invention display very strong adhesion to the nail, good wear, resistance to damage and gloss.

Without being bound by theory, it is believed that cross-linking between the inventive film formers comprising polycarbodiimide and latex improve adhesion of the inventive nail compositions as compared to other latex based nail compositions in the art. The unique combination of properties of the invention compositions deliver nail compositions which consumers can wear and which undergo further crosslinking over time, from one to 5 days, to provide resistance to damage for an extended period, good gloss and adhesion, and which are removed with ease as compared to other latex nail compositions.

According to the various embodiments, the compositions comprising polycarbodiimide and latex may contain any one or combination of solvents, adhesives, plasticizers, secondary and co-film formers, thixotropic agents/rheology modifiers, fillers, pigments, and other additives such as preservatives, defoamers, and others known in the art.

Solvents

According to some embodiments, the compositions of the present invention may also optionally include at least one solvent chosen from organic and inorganic solvents. Suitable solvents may particularly be chosen from:liquid ketones at ambient temperature such as methylethylketone, methylisobutylketone, diisobutylketone, isophorone, cyclohexanone and acetone, liquid alcohols at ambient temperature such as ethanol, isopropanol, diacetone-alcohol, 2-butoxyethanol and cyclohexanol, liquid glycols at ambient temperature such as ethyleneglycol, propyleneglycol, pentyleneglycol and glycerol, liquid propyleneglycol ethers at ambient temperature such as propyleneglycol monomethylether, propyleneglycol monomethyl ether acetate and dipropyleneglycol mono-n-butylether, short-chain esters (comprising in total from 3 to 8 carbon atoms) such as ethyl acetate, methyl acetate, propyl acetate, n-propyl acetate, iso-propyl acetate, n-butyl acetate, iso-butyl acetate, ter-butyl acetate and isopentyl acetate, liquid alkanes at ambient temperature such as decane, heptane, dodecane and cyclohexane, liquid aromatic hydrocarbons at ambient temperature such as toluene and xylene, liquid silicones at ambient temperature, and mixtures thereof.

The compositions according to the invention may also comprise so-called volatile solvents. The term "volatile solvent" refers to a solvent capable of evaporating on contact with keratin matter, in less than one hour, at ambient temperature and at atmospheric pressure.

The volatile solvents according to the invention are In some embodiments liquid solvents at ambient temperature, having a vapor pressure different to zero, at ambient temperature and atmospheric pressure, particularly ranging from 0.13 Pa to 40,000 Pa (from $10^{-3}$ to 300 mm Hg), particularly ranging from 1.3 Pa to 13,000 Pa (from 0.01 to 100 mm Hg), and more specifically ranging from 1.3 Pa to 1300 Pa (from 0.01 to 10 mm Hg).

On the other hand, a "non-volatile solvent" evaporates on contact with keratin matter in more than one hour, at ambient temperature and atmospheric pressure.

In some embodiments, the compositions of the present invention comprise a solvent chosen from acetone, ethyl acetate, propyl acetate, butyl acetate, isopropyl alcohol, and mixtures thereof.

In some embodiments, the total solvent content in the inventive nail compositions is above about 15%, in some embodiments above about 20%, and in some embodiments above about 30% by weight in relation to the total weight of the composition.

Adhesive Agents

In accordance with the present invention, nail compositions comprising at least one adhesive agent are provided. In some embodiments, the adhesive agent is chosen from the group consisting of radical or polycondensate type synthetic polymers, polymers of natural origin, and mixtures thereof.

In some embodiments, the adhesive agent is chosen from polysaccharide derivatives, such as cellulose or guar gum derivatives. In some embodiments polysaccharide derivatives include nitrocellulose or a polysaccharide ester or alkylether. The term "polysaccharide ester or alkylether" refers to a polysaccharide consisting of repeat units comprising at least two identical or different rings and having a degree of substitution per saccharide unit between 1.9 and 3, in some embodiments between 2.2 and 2.9, and more particularly between 2.4 and 2.8. The term substitution refers to the functionalization of hydroxyl groups into ester and/or alkylether functions, and/or the functionalization of carboxyl groups into ester functions.

In other words, it may consist of a polysaccharide, partially or totally substituted with ester and/or alkylether groups. In some embodiments, the hydroxyl groups may be substituted with $C_2$-$C_4$ ester and/or alkylether functions.

Particular mention may be made of cellulose esters (such as cellulose acetobutyrates or cellulose acetopropionates), cellulose alkylethers (such as ethylcelluloses), and ethylguars.

In some embodiments, the at least one adhesive agent is present in the nail compositions of the present invention at a total content greater than or equal to 0.1%, in some embodiments from about 0.2% to about 25%, in some embodiments from about 1% to about 20%, preferentially from about 3% to about 18%, by weight in relation to the total weight of the composition.

Plasticizers

In accordance with the present invention, nail compositions comprising at least one plasticizer are provided. Generally speaking, plasticizers are additives used to optimize the mechanical properties of films. They tend to reduce the Glass Transition Temperature (Tg) and increase the softness and flexibility of the films.

In some embodiments, suitable plasticizers have a boiling point measured at ambient pressure of less than or equal to 285° C., in some embodiments less than or equal to 270° C., and in some embodiments less than or equal to 250° C. In the present specification, the boiling point values are to be considered accurate to ±2° C. owing to the uncertainties of boiling point measurement.

Any plasticizing agent typically found in nail polish compositions can be used. Examples of suitable plasticizers include, but are not limited to, glycols and their ester derivatives, esters of acids, in particular carboxylic acids, such as citrates, adipates, carbonates, tartrates, phosphates or sebacates, oxyethylenated derivatives, such as oxyethylenated oils, and their mixtures. For example, suitable plasticizing agents include, but are not limited to, diisobutyl adipate, the ester of teributyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, ethyl tosylamide and mixtures thereof.

In some embodiments, the plasticizer is in some embodiments present in the composition in an amount from about 0.1% to about 25% by weight, in some embodiments from about 0.5% to about 20% by weight, in some embodiments from about 1% to about 10% by weight, of the total weight of the composition, including all ranges and subranges there between.

Secondary Film Formers

In accordance with the present invention, nail compositions comprising at least one secondary film forming agent are provided. Some examples of secondary film former agents include but are not limited to acrylic polymers (homopolymers or copolymers), in some embodiments in the form of solid powders (flakes) and solvent free. Specific examples of suitable secondary film formers include:

Synthetic polymers of the polycondensate type or of the free-radical type;

Acrylic polymers resulting from the copolymerization of monomers chosen from the esters and/or amides of acrylic acid and/or of methacrylic acid. As examples of monomers of ester type, mention may be made of methyl methacrylate, ethyl methacrylate, butyl methacrylate, isobutyl methacrylate, 2-ethylhexyl methacrylate and lauryl methacrylate. As examples of monomers of amide type, mention may be made of N-t-butylacrylamide and N-t-octylacrylamide; and Acrylic polymers obtained by copolymerization of ethylenically unsaturated monomers containing hydrophilic groups, in some embodiments of nonionic nature, such as hydroxyethyl acrylate, 2-hydroxypropyl acrylate, hydroxyethyl methacrylate and 2-hydroxypropyl methacrylate.

Generally speaking, the secondary film-forming polymers may be chosen from synthetic polymers such as polyurethanes, acrylic polymers, styrene acrylate copolymers, acrylate silicone copolymers, vinyl polymers, polyvinylbutyrals, alkyd resins, ketone/aldehyde resins, and resins from aldehyde condensation products, such as aryl sulfonamide formaldehyde resins such as toluene or sulfonamide formaldehyde resin.

According to some embodiments of the invention, the secondary film forming agent is selected from carboxyl functional acrylate polymers having a moderate to high glass transmission temperature (Tg) value. The "moderate to high glass transmission" as used in the context of the present invention, refers to an acrylates copolymer having Tg value ranging from about 40° C. to about 95° C., in some embodiments from about 60° C. to about 90° C., and in some embodiments from about 70° C. to about 85° C.

According to some embodiments, the secondary film forming agent has a relatively high acid value, such as for example an acid value (number) ranging from about 40 to about 95, In some embodiments from about 50 to about 90, and in some embodiments from about 60 to about 80, including all ranges and subranges therebetween.

Commercially available examples of the secondary film forming polymers include but are not limited to, for example, those sold under the Isocryl® name by Estron Chemicals such as, for example, Isocryl C-70 (styrene/acrylates copolymer), Isocryl N-2513, Isocryl H-60, and Isocryl H-1871.

In some embodiments, the secondary film former(s) are present in the compositions of the present invention in amounts ranging from about 0.5% to about 20% by weight, in some embodiments from about 1% to about 15%, and in some embodiments from about 2% to about 10%, by weight, based on the total weight of the composition, including all ranges and subranges in between.

According to some embodiments, the compositions of the present invention may also optionally include at least one secondary film forming agent chosen from epoxy resins. Suitable examples of epoxy resins include those disclosed in U.S. Pat. No. 5,001,175, the entire contents of which is hereby incorporated by reference.

In some embodiments, suitable epoxy resins have a glass transition temperature (Tg) of less than about 100° C., in some embodiments less than about 80° C. Non-limiting examples of suitable epoxy resins include tosylamide epoxy resins, such as those sold by Estron Chemical under the tradename Polytex™, e.g., E-75, E-100, and NX-55, NX-3214). Other non-limiting examples of suitable epoxy resins include arylsulfonamide epoxy resins.

According to some embodiments, if present, the at least one secondary film former is present in the invention compositions in an amount ranging from about 0.1% to about 50% by weight, in some embodiments from about 1% to about 40% by weight, and in some embodiments from about 3% to about 15% by weight, including all ranges and subranges therebetween, all weights being based on the total weight of the composition.

Co-Film Formers

According to some embodiments, the compositions of the present invention may also optionally include at least one co-film forming agent. Suitable co-film forming agents include, but are not limited to, (meth)acrylate homopolymers and copolymers, polyurethanes, polyacryls, polymethacryls, cellulosic polymers, styrene-acryl copolymers, polystyrene-polyacryl mixtures, polysiloxanes, polyethers, polyesters, urethane-acryl copolymers, cellulose acetate propionate, siloxane-urethane copolymers, polyurethane-polymethacryl mixtures, silicone-acryl copolymers, vinyl acetate polymers, and mixtures thereof.

Suitable co-film forming agents also include aldehyde condensation products such as arylsulfonamide formaldehyde resins, specifically toluene sulfonamide formaldehyde resin which is a condensation product of formaldehyde and toluene sulfonamide, toluene sulfonamide/epoxy resins, e.g. tosylamide and non-drying alkyd resins, acrylic polymers and copolymers, polyurethane, polyacryls, polymethacryls, styrene-acryl copolymers, polystyrene-polyacryl mixtures, polysiloxanes, polyethers, polyesters, urethane-acryl copolymers, siloxane-urethane copolymers, polyurethane-polymethacryl mixtures, vinyl acetate polymers, and mixtures thereof.

Suitable co-film forming agents also include polyester resins formed by reacting a polyhydric alcohol with a polybasic acid, e.g., phthalic acid, such as the commercial product sold by Unitex Chemical Corporation under the name UNIPLEX 670-P, which is a polyester resin obtained by reacting trimellitic acid, neopentyl glycol, and adipic acid. (Meth)acrylic resins according to the disclosure may include copolymers of methyl methacrylate with butyl acrylate, butyl methacrylate, isobutyl methacrylate, or isobornyl methacrylate, for example, the commercial products PARALOID DM-55, PARALOID B48N, PARALOID B66, and ELVACITE 2550; copolymers of isobutylmethacrylate and butyl methacrylate, for instance, the commercial product ELVACITE 2046; and isobutyl methacrylate polymers, for example, PARALOID B67.

Suitable co-film forming agents also include polymers of natural origin, such as plant resins such as dammars, elemi, copals, benzoin; gums such as shellac, sandarac and mastic.

Specific examples of suitable co-film forming agents include, but are not limited to phthalic anhydride/glycerin/glycidyl decanoate copolymer, adipic acid/neopenttyl glycol/trimellitic anhydride copolymer, tosylamide/epoxy resin, butyl acetate (and) acrylates copolymer, and hydrogenated acetophenone/oxymethylene copolymer.

In some embodiments, present the at least one co-film forming agents are added to the nail compositions of the present invention in an amount ranging from about 0.1 to 10 percent, in some embodiments from about 0.2 to 8 percent, in some embodiments from about 0.5 to about 5 percent by weight of the total weight of the composition, including all ranges and subranges there between.

Silicone Acrylate Copolymer

According to some embodiments, the compositions of the present invention may also optionally include at least one silicone acrylate copolymer.

In some embodiments, suitable silicone acrylate copolymers have a glass transition temperature (Tg) of greater than 20° C., in some embodiments greater than about 25° C.

Suitable examples of silicone acrylate copolymers include silicone/(meth)acrylate copolymers, such as those described in U.S. Pat. Nos. 5,061,481, 5,219,560, 5,262,087 and US 2012/0301415, the entire contents of all of which are hereby incorporated by reference.

Suitable examples also include polymers derived from non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the products sold under the tradenames KP-545 (cyclopentasiloxane (and) acrylates/dimethicone copolymer), KP-543 (butyl acetate (and) acrylates/dimethicone copolymer), KP-549 (methyl trimethicone (and) acrylates/dimethicone copolymer), KP-550 (tentative INCI name: isododecane (and) acrylate/dimethicone copolymer), and mixtures thereof. Additional examples include the acrylate/dimethicone copolymers sold by Dow Corning under the tradenames FA 4001 CM SILICONE ACRYLATE (cyclopentasiloxane (and) acrylates/polytrimethylsiloxymethacrylate copolymer) and FA 4002 ID SILICONE ACRYLATE (isododecane (and) acrylates/polytrimethylsiloxymethacrylate Copolymer), and mixtures thereof.

Suitable examples also include polymers comprising a backbone chosen from vinyl polymers, methacrylic polymers, and acrylic polymers, and at least one chain chosen from pendant siloxane groups. Non-limiting examples of such polymers and their synthesis are disclosed, for example, in U.S. Pat. Nos. 4,972,037, 5,061,481, 5,209,924, 5,849,275, and 6,033,650, and WO 93/23446, WO 95/06078 and WO 01/32737, the disclosures of all of which are hereby incorporated by reference. These polymers may be sourced from various companies. One such company is Minnesota Mining and Manufacturing Company which offers these types of polymers under the tradenames "Silicone Plus" polymers (for example, poly(isobutyl methacrylate-comethyl FOSEA)-g-poly(dimethylsiloxane), sold under the tradename SA 70-5 IBMMF).

Suitable examples also include silicone/acrylate graft terpolymers, for example, the copolymers described in WO 01/32727 A1, the disclosure of which is hereby incorporated by reference.

Suitable examples also include polymers comprises a backbone chosen from vinyl backbones, methacrylic backbones, and acrylic polymeric backbones and further comprises at least one pendant siloxane group. Non-limiting examples of such polymers are disclosed in U.S. Pat. Nos. 4,693,935, 4,981,903, and 4,981,902, the disclosures of which are hereby incorporated by reference.

Suitable examples also include those described in U.S. Pat. No. 5,468,477, the disclosure of which is hereby incorporated by reference. A non-limiting example of these polymers is poly(dimethylsiloxane)-g-poly(isobutyl methacrylate), which is commercially available from 3M Company under the tradename VS 70 IBM.

In some embodiments, if present, the at least one silicone acrylate copolymer is present in the compositions of the present invention in an amount ranging from about 0.1 percent to about 10 percent by weight, in some embodiments from about 0.5 percent to about 8.5 percent, and in some embodiments from about 0.25 percent to about 5 percent by weight, including all ranges and subranges therebetween, all weights being based on the total weight of the composition.

Thixotropic Agent

According to some embodiments, the compositions of the present invention may also optionally include at least one thixotropic agent in an amount that is sufficient to give the composition a viscosity at rest sufficient to give it the desired texture and thixotropic behavior.

In at least one embodiment, the nature and/or amount of the at least one thixotropic agent is such that, in response to a non-chemical action, for instance, a mechanical action, prior to or simultaneously with the application of the composition to the nails, the viscosity of the composition may be reversibly lowered to a value less than or equal to 0.4 Pa·s, for example, less than or equal to 0.3 Pas.

The at least one thixotropic agent may be chosen, for example, from hydrophilic or organophilic clays, hydrophilic or hydrophobic fumed silicas, elastomeric organopolysiloxanes, and mixtures thereof.

Clays are silicates containing a cation that may be chosen from calcium, magnesium, aluminium, sodium, potassium, and lithium cations, and mixtures thereof. As used herein, the term "hydrophilic clay" means a clay that is capable of swelling in water; this clay swells in water and forms after hydration a colloidal dispersion.

Examples of such products include, but are not limited to, clays of the smectite family such as montmorillonites, hectorites, bentonites, beidellites, and saponites, clays of the vermiculite family, stevensite, and chlorites.

These clays may be of natural or synthetic origin.

Non-limiting examples of hydrophilic clays include smectites such as saponites, hectorites, montmorillonites, bentonites, beidellite and, in at least one embodiment, synthetic hectorites (also known as laponites), for instance, the products sold by the company Laporte under the names Laponite XLG, Laponite RD, and Laponite RDS (these products include, for example, sodium magnesium silicates and sodium lithium magnesium silicates); bentonites, for instance the product sold under the name Bentone HC by the company Rheox; magnesium aluminium silicates, which may be hydrated, for instance, the products sold by the company Vanderbilt Company under the names Veegum Ultra, Veegum HS, and Veegum DGT, and calcium silicates, such as the product in synthetic form sold by the company under the name Micro-cel C.

The organophilic clays are clays modified with chemical compounds that make the clay capable of swelling in solvent media.

The clay may be chosen, for example, from montmorillonite, bentonite, hectorite, attapulgite, sepiolite, and mixtures thereof. In one embodiment, the clay is chosen from bentonite and hectorite.

The chemical compound used to modify the organophilic clay may be chosen, for instance, from quaternary amines, tertiary amines, amine acetates, imidazolines, amine soaps, fatty sulfates, alkyl aryl sulfonates, amine oxides, and mixtures thereof.

Suitable organophilic clays include, but are not limited to, quaternium-18 bentonites such as those sold under the names Bentone 3, Bentone 38, Bentone 27 V CG, and Bentone 38V by the company Elementis, Tixogel VP by the company United Catalyst, and Claytone 34, Claytone 40, and Claytone XL by the company Southern Clay; stearalkonium bentonites such as those sold under the names Bentone 27V by the company Elementis, Tixogel LG by the company United Catalyst, and Claytone AF and Claytone APA by the company Southern Clay; and quaternium-18/benzalkonium bentonites such as those sold under the names Claytone HT and Claytone PS by the company Southern Clay.

The hydrophilic fumed silicas may be obtained by high-temperature hydrolysis of a volatile silicon compound in an oxyhydric flame, producing a finely divided silica. Hydrophilic silicas have a large number of silanol groups at their surface. Such hydrophilic silicas are sold, for example, under the names Aerosil 130(R), Aerosil 200(R), Aerosil 255(R), Aerosil 300(R), and Aerosil 380(R) by the company Degussa, and Cab-O-Sil HS-5(R), Cab-O-Sil EH-5(R), Cab-O-Sil LM-130(R), Cab-O-Sil MS-55(R), and Cab-O-Sil M-5(R) by the company Cabot.

The hydrophobic fumed silicas may be obtained by modification of the surface of the silica via a chemical reaction that generates a reduction in the number of silanol groups, these groups possibly being substituted, for example, with hydrophobic groups.

The hydrophobic groups may be chosen, for instance, from: trimethylsiloxyl groups, which may be obtained by treating fumed silica in the presence of hexamethyldisilazane. Silicas thus treated are known as "Silica silylate" according to the CTFA (6th edition, 1995). They are sold, for example, under the references Aerosil R812(R) by the company Degussa, and Cab-O-Sil TS-530(R) by the company Cabot, dimethylsilyloxyl or polydimethylsiloxane groups, which may be obtained by treating fumed silica in the presence of polydimethylsiloxane or dimethyldichlorosilane. Silicas thus treated are known as "Silica dimethyl silylate" according to the CTFA (6th edition, 1995). They are sold, for example, under the references Aerosil R972(R) and Aerosil R974(R) by the company Degussa, and Cab-O-Sil TS-610(R) and Cab-O-Sil TS-720(R) by the company Cabot.

According to one embodiment, the at least one thixotropic agent is chosen from organophilic modified clays such as hectorite modified with benzyldimethylammonium stearate.

The thixotropic agent, if present, may be present in the composition in an amount greater than or equal to 0.05 percent by weight, for example, ranging from 0.05 percent to 15 percent by weight, or greater than or equal to 0.5 percent by weight, for example, ranging from 0.5 percent to 10 percent by weight, or ranging from 0.9 percent to 7.5 percent by weight, relative to the total weight of the composition, including all ranges and subranges therebetween.

Fillers

According to some embodiments, the compositions of the present invention may also optionally include at least one filler. Suitable examples of fillers include mineral or organic particles of any shape, in sheet, spherical or oblong form, regardless of the crystallographic shape (for example sheet, cubic, hexagonal, orthorhombic, etc). Mention may be made of talc, mica, kaolin, polyamide (Nylon®) (Orgasol® from Atochem), poly-β-alanine and polyethylene powders, tetrafluoroethylene polymer powders (Teflon®), lauroyl-lysine, starch, boron nitride, acrylic acid copolymers (Polytrap® from Dow Corning) and silicone resin microbeads (Tospearls® from Toshiba, for example), elastomer polyorganosiloxane particles, precipitated calcium carbonate, magnesium carbonate and hydro-carbonate, hydroxyapatite, glass or ceramic microcapsules, metallic soaps derived from carboxylic organic acids having 8 to 22 carbon atoms, in some embodiments from 12 to 18 carbon atoms, for example zinc, magnesium or lithium stearate, zinc laurate, magnesium myristate.

Fillers, if present, can be present particularly at a content ranging from about 0.01% to about 10% by weight, in some embodiments ranging from about 0.1% to about 5% by weight, in some embodiments from about 0.5% to about 1.5%, in relation to the total weight of the inventive compositions, including all ranges and subranges therebetween.

Coloring Agent

According to some embodiments, the compositions of the present invention may also optionally include at least one coloring agent. In some embodiments, the at least one coloring agent is chosen from the group consisting of soluble dyes, pigments, nacres and glitter.

The term "soluble dyes" should be understood to refer to organic, inorganic or organometallic compounds, soluble in the composition according to the invention and intended to color said composition.

Suitable dyes are, for example, Sudan Red, DC Red 17, DC Green 6, β-carotene, soybean oil, Sudan brown, DC Yellow 11, DC Violet 2, DC Orange 5 and Quinoline Yellow.

The term "nacres" should be understood to refer to iridescent particles of any shape, particularly produced by some mollusks in their shell or by synthetic means.

The term "pigments" should be understood to refer to inorganic or organic, white or colored particles of any shape, insoluble in the composition according to the invention and intended to color said composition.

The pigments may be white or colored, inorganic and/or organic. Of the inorganic pigments, mention may be made of titanium dioxide, optionally surface-treated, zirconium or cerium oxides, along with zinc, iron (black, yellow or red) or chromium oxides, manganese violet, ultramarine blue, chromium hydrate and iron blue, metallic powders such as aluminum powder, copper powder.

Of the organic pigments, mention may be made of carbon black, D & C type pigments, and lacquers based on cochineal carmine, barium, strontium, calcium, aluminum.

Mention may also be made of effect pigments such as particles comprising a natural or synthetic organic or inorganic substrate, for example glass, acrylic resins, polyester, polyurethane, polyethylene terephthalate, ceramics, aluminas and optionally coated with metallic substances such as aluminum, gold, copper, bronze, or with metal oxides such as titanium dioxide, iron oxide, chromium oxide, inorganic or organic pigments and mixtures thereof.

The pearlescent pigments may be chosen from white pearlescent pigments such as mica coated with titanium, or bismuth oxychloride, colored pearlescent pigments such as titanium mica coated with iron oxides, titanium mica coated with iron blue and chromium oxide in particular, titanium mica coated with an organic pigments of the aforementioned type and pearlescent pigments based on bismuth oxychloride.

Pigments with goniochromatic properties may be used, particularly liquid crystal or multilayer pigments.

Optical brighteners or fibers optionally coated with optical brighteners may also be used.

The at least one coloring agent, if present, is In some embodiments present in a total content greater than or equal to 0.1% by weight in relation to the total weight of the layer, ranging In some embodiments from about 0.1 to about 5%, advantageously from about 0.2 to about 3% by weight in relation to the total weight of the composition, including all ranges and subranges therebetween.

Auxiliaries/Additives

According to some embodiments, the compositions of the present invention may also optionally include at least one additive or auxiliary commonly used in cosmetic compositions and known to a person skilled in the art as being capable of being incorporated into said compositions. Such additives or auxiliaries may be chosen from preservatives, fragrances, oils, waxes, surfactants, antioxidants, agents for combating free radicals, spreading agents, wetting agents, dispersing agents, antifoaming agents, neutralizing agents, stabilizing agents, active principles chosen from essential oils, UV screening agents, sunscreens, moisturizing agents, vitamins, actives, proteins, ceramides, plant extracts, fibers, and the like, wetting agents and their mixtures.

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the color coat or top coat composition in a proportion from about 0% to about 10%, such as from about 0.01% to about 7% relative to the total weight of the composition and further such as from about 0.1% to about 5%, including all ranges and subranges therebetween.

Needless to say, the composition of the invention should be cosmetically or dermatologically acceptable, i.e., it should contain a non-toxic physiologically acceptable. The composition may be in any galenic form normally employed in the cosmetic and dermatological fields which is suitable for topical administration onto nails.

According to some embodiments of the present invention, methods for making up and/or protecting nails comprising applying to the nails at least one nail composition of the present invention in an amount sufficient to makeup or protect the nails are provided.

According to some embodiments of the present invention, methods for making a nail composition comprising combining at least one adhesive agent; at least one secondary film former; and at least one plasticizer in a nail composition are provided.

The following Examples are intended to be non-restrictive and explanatory only, with the scope of the invention being defined by the claims.

Raw Materials Employed in the Examples

| Designations | Ingredient Information |
|---|---|
| Latex | Acrylates Copolymer (INCI name); Commercially available as DAITOSOL 3000SLPN from the supplier Daito Kasei Kogyo (30% active) |
| Polycarbodiimide SV02 ("pCDI SV02") | Commercially available as CARBODILITE SV-02 from the supplier Nisshinbo (40% active) |
| Polycarbodiimide V-02-L2 | Commercially available as CARBODILITE V-02-L2 from the supplier Nisshinbo (40% active) |
| Dispersant | Sodium Polymethacrylate (25% active in water) |
| Deformer | INCI name: DIMETHICONE (and) POLYSORBATE 65 (and) SIMETHICONE, commercially available as Xiameter AFE-1510 from Dow corning |

Preparation

Red 7 Pigment Paste

First, a Red 7 pigment paste was formulated using the components shown in the table below. All components were mixed using a disconti mill.

TABLE 1

| INCI name | Weight % | Weight % (AM*) |
|---|---|---|
| Water | 74.525 | QS |
| Red 7 | 15 | 15 |
| dispersant | 9.375 | 2.34 |
| deformer | 0.1 | 0.1 |
| Phenoxyethanol | 1 | 1 |

*AM = active material

Carbodiimide-Based Nail Enamel

The components listed in TABLE 2 were added to a high speed mixture cup and mixed at 2500 RPM for 2 min.

TABLE 2

| INCI name | Weight % | Weight % (AM*) |
|---|---|---|
| latex | 73.8 | 22.14 |
| Polycarbodiimide SV-02 | 18.4 | 7.36 |
| phenoxyethanol | 1 | 1 |
| Red 7 Paste | 6.7 | 6.7 |
| Deformer | 0.1 | 0.1 |
| Water | QS | QS |

Adhesion, Tack and Flexibility Test

Samples (3 g) were added to a polystyrene weight boat and allowed to dry overnight. The adhesion, tack and flexibility of the samples were measured by touching, peeling and bending the samples in hand.

Stability

The stability of the formulations was measured over an eight week period. Every week, the samples would be removed from the 45° C. oven and assessed. The rheology profile of the samples were determined visually and using a Rheometer.

Hardness Test

A film was drawn down using a 3 MIL draw down bar onto a thin glass substrate. After the film was dry, the hardness was measured using the BYK pencil hardness test.

Shine Test

Shine was determined using a gloss meter. For this determination, a layer of the composition to be tested was spread on a contrast card using an automatic spreader. The layer covered at least the white background of the card. The film was allowed to dry. The gloss was measured at 20° using a Byk Gardner gloss meter of reference microTRI-GLOSS. This measurement was repeated 3 times, and the average gloss (in gloss units (GU)) is the average of the 3 measurements carried out.

Removal of Water Based Nail Enamel

One color coat of aqueous nail enamel was layered onto a nail spoon. After three minutes, a second color coat was layered on top of the first. After drying for 24 hours at 40° C., the enamel can be removed with any conventional acetone-based nail enamel faster than other water based nail enamels (see Table 2).

EXAMPLES

Selected waterborne latexes were screened by adding a small amount of polycarbodiimide and determine if chemical crosslinking is occurring.

Two different polycarbodiimides (Carbodilite SV-02 and Carbodilite V02-L2) were mixed with ten different carboxylic acid functionalized latexes at 1:1 ratio to determine if crosslinking occurs and if adhesion is increased compared to the latex alone. Out of the 10 different latexes, four showed the most promise in terms of improved adhesion after mixing with the polycarbodiimides. Out of the four promising candidates, Daitosol 3000 SLPN showed the greatest increase in adhesion when mixed with Carbodilite SV-02 compared to Daitosol 3000 SLPN latex alone.

Active compounds in the nail enamel were varied, specifically Daitosol 3000 SLPN to Carbodilite SV-02, to determine performance as compared to 1:1 ratios of Daitosol 3000 SLPN to Carbodilite SV-02. Ratios of 90:10, 80:20, 70:30 and 60:40 by weight Daitosol 3000 SLPN to Carbodilite SV-02 were tested. The film properties were assessed and ranked: Adhesion (5 is best adhesion, 0 is no adhesion); stickiness (5 is no sticky, 0 is very sticky); Flexibility (5 is very flexible, 0 is no flexibility), Removal (5 is easiest removal, 0 is the most difficult to remove) On a scale of 1 to 5, with 5 being the best, 80:20 Daitosol 3000 SLPN/Carbodilite SV-02 showed the greatest adhesion, with the least tack and moderate flexibility (Table 3). The combination of the polycarbodiimide and latex was shown to dramatically increase the adhesion and decrease the tackiness.

TABLE 3

In vitro properties of different weight ratios of Daitosol 3000 SLPN/Carbodilite SV-02 (active percentage shown in parentheses)

| Sample (active concentration) | Adhesion | Sticky | Flexibility | Removal |
|---|---|---|---|---|
| 70:30 Daitosol 3000 SLPN to Carbodilite SV-02 (21% to 12%) | 4 | 5 | 5 | 4 |
| 80:20 Daitosol 3000 SLPN to Carbodilite SV-02 (24% to 8%) | 5 | 5 | 3 | 5 |
| 90:10 Daitosol 3000 SLPN to Carbodilite SV-02 (27% to 4%) | 5 | 5 | 2 | 5 |
| Daitosol 3000 SLPN | 2 | 4 | 5 | 5 |
| Carbodilite SV-02 | 3 | 1 | 5 | 5 |

To determine if the 80:20 Daitosol 3000 SLPN/Carbodilite SV-02 mixture within the film was, cross-linked or if a cohesive mixture of separate polymers was being formed, Fourier-transform infrared (FT-IR) spectroscopy was used. A carboxylic acid functionalized waterborne latex (Daitosol 3000 SLPN, 80% by weight) was added to a polycarbodiimide (Carbodilite SV-02, 20% by weight) and draw down a film, the film was dried and cross-linked to form an acyl-urea derivative. Confirmation of crosslinking was achieved by measuring the FT-IR stretch (data not shown) of polycarbodiimide (R—N═C═N—R). As measured over time from Day 1 to Day 6 at room temperature, the peak decreased in size compared to all other peaks in the spectrum, indicating that the polycarbodiimide bond is reacting with the carboxylic acid (R1-COOH) to form a cross-linked product (R1-C(═O)—N(—R)—CO—NH—R).

Based on the obtained results, a nail enamel was formulated containing an 80:20 ratio of Daitosol 3000 SLPN and Carbodilite SV-02, as the primary film formers, to which was also added a pigment paste that contains sodium polymethacrylate to aid in pigment dispersion, an antifoaming agent and preservatives. Optional additives include plasticizers, coalescent, other film formers that do not contain carboxylic acid groups, thickening agents, nanoparticles, perfumes, silicones, neutralizing agents and active agents for nail care. Table 4 shows a comparison of the in vitro properties of a traditional solvent-based (nitrocellulose) nail enamel (Market Bench 1), water based nail enamel containing latex (Comparative 1), and the Carbodiimide water based nail enamel (Inventive 1). Inventive 1 shows excellent in vitro properties compared to latex water based nail enamel. It was observed with the inventive polycarbodiimide nail enamel that stability at 45° C. could be compromised due to reactive crosslinking under elevated temperatures, resulting in gelling.

TABLE 4

In-vitro properties of a traditional SB (Solvent-based) nail enamel (Market Bench 1), a latex water based (WB) nail enamel (Market Bench 2), a Latex WB nail enamel (Comparative 1) and a Carbodiimide WB nail enamel (Inventive 1).

| Formula | Adhesion | Shine (GUs, 20°) | Hardness 2H = 5 | Contact Angle ($H_2O$) | Wear Evaluation | Removal (No. of strokes w/ acetone) | Stability (45° C., 60 days) |
| --- | --- | --- | --- | --- | --- | --- | --- |
| Market Bench 1 (SB, 2 coats) | 5 | 58.1 | 5 | 83.1 | 4-5 days | 5 | Good |
| Market Bench 2 (WB, 2 coats) | | | | | | 30 | |
| Comparative 1 (WB, 2 coats) | 5 | 32.3 | 5 | 52.8 | 3-5 days | 25 | Good |
| Inventive 1 (WB, two coats) | 5 | 55.3 | 4 | 70.8 | | 12 | Gel |

Most latexes, when dry, are very difficult to remove (may take up to 5 minutes per hand) compared to traditional solvent based nail enamel (less than one minute per hand). Removability was assessed of Inventive 1 versus different Market Benchmarks (solvent and water-based) and one comparative water based formula. All formulas were applied to nail spoons (two color coats) and allowed to dry overnight. The nail enamel was removed using a cotton pad w/0.5 mL of acetone. The number of strokes needed to remove most of the nail enamel was recorded and shown in Table 4. Inventive 1 shows excellent removal properties (12 strokes) compared to another latex water based nail enamel (Comparative 1, 25 strokes) and a Market Bench water based nail enamel (30 strokes). Solvent-based market bench is used as a control and only takes 5 strokes to remove the nail enamel. Inventive 1 shows excellent removal properties because the carboxylic acid functionalized latex (Daitosol 3000 SLPN) used in the inventive composition is very sensitive to solvent based removal.

While the invention has been described with reference to exemplary and some embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A nail composition comprising:
   at least one primary nail film former comprising
   a latex compound comprising an acrylate latex polymer; and
   a polycarbodiimide compound comprising a carbodiimide polymer or copolymer and having the following formula:

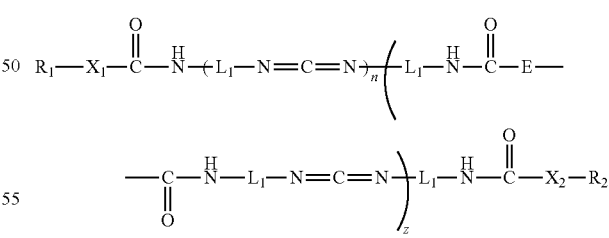

wherein $X_1$ and $X_2$, each independently, represents O, S or NH; $R_1$ and $R_2$, each independently, represent a hydrocarbon group containing one or more catenary or non-catenary hetero-atoms and containing linear or branched and cyclic or acyclic groups which are ionic or non-ionic segments or a partially or fully fluorinated hydrocarbon group containing one or more catenary or non-catenary hetero-atoms; n and z are, each independently, an integer of 0 to 20, wherein one or both of n or z is a positive integer; $L_1$ represents a $C_1$ to $C_{18}$ divalent aliphatic hydrocarbon group, a $C_3$ to $C_{13}$ divalent alicyclic hydrocarbon group, a $C_6$ to $C_{14}$ divalent aromatic hydrocarbon group, a $C_3$ to $C_{12}$ divalent heterocyclic group, or a $C_6$ to $C_{14}$ divalent aromatic hydrocarbon group that does not comprise tetramethylxylylene, wherein a plurality of $L_1$ groups may be identical to or different from one another; E is a radical selected from the group consisting of:

O—$R_3$—O;S—$R_4$—S; and $R_5$—N—$R_4$—N—$R_5$;

wherein $R_3$ and $R_4$ are, each independently, hydrocarbon radicals that may contain halogen atoms or one or more catenary or non-catenary hetero atoms, including an aromatic, cycloaliphatic, aryl and linear or branched alkyl radical and $R_5$ is hydrogen or a hydrocarbon radical, the hydrocarbon radical, when present, includes halogen atoms or one or more catenary or non-catenary hetero atoms;

wherein the ratio, based upon the weight of each compound, of the latex compound to the polycarbodiimide compound is in the range from about 50:50 to about 80:20; and wherein the composition comprises from about 10% to about 95%, by weight, based upon the total weight of the composition, of a combined amount of the polycarbodiimide compound and the latex compound, and has at least moderate flexibility when cured.

2. A nail composition according to claim 1, further comprising at least one solvent.

3. A nail composition according to claim 1, further comprising at least one adhesive agent.

4. A nail composition according to claim 1, further comprising at least one secondary film former.

5. A nail composition according to claim 1, wherein the ratio, based upon the weight of each compound, of the latex compound to the polycarbodiimide compound is in the range from about 70:30 to about 80:20.

6. A nail composition according to claim 1, wherein the ratio, based upon the weight of each compound, of the latex compound to the polycarbodiimide compound is about 80:20.

7. A nail composition according to claim 1, wherein the latex compound is formed from monomers selected from the group consisting of acrylic acid, methacrylic acid, and esters and amides thereof.

8. A nail composition according to claim 7, wherein the latex compound is formed from a monomer selected from the group consisting of an acrylic acid-based monomer and a (meth)acrylic acid-based monomer.

9. A nail composition according to claim 1, wherein the ratio, based upon the weight of each compound, of the latex compound to the polycarbodiimide compound is about 70:30.

10. A nail composition according to claim 1, wherein the composition comprises from about 10% to about 60%, by weight, based upon the total weight of the composition, of a combined amount of the polycarbodiimide compound and the latex compound.

11. A nail composition according to claim 1, wherein the composition comprises from about 20% to about 40%, by weight, based upon the total weight of the composition, of a combined amount of the polycarbodiimide compound and the latex compound.

12. A nail composition according to claim 1, wherein the composition comprises about 30%, by weight, based upon the total weight of the composition, of a combined amount of the polycarbodiimide compound and the latex compound.

13. A nail composition according to claim 1, wherein the ratio, based upon the weight of each compound, of the latex compound to the polycarbodiimide compound is from about 70:30 to about 80:20, and wherein the composition comprises about 30%, by weight, based upon the total weight of the composition, of a combined amount of the polycarbodiimide compound and the latex compound.

14. A nail composition comprising:
at least one primary nail film former comprising
a latex compound comprising an acrylate latex polymer; and
a polycarbodiimide compound comprising a carbodiimide polymer or copolymer having the following formula:

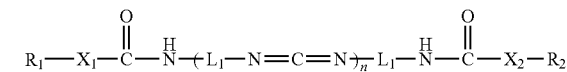

wherein $X_1$ and $X_2$, each independently, represents O, S or NH; $R_1$ and $R_2$, each independently, represent a hydrocarbon group containing one or more catenary or non-catenary hetero-atoms and containing linear or branched and cyclic or acyclic groups; n is an integer of 2 to 20; $L_1$ represents one of a $C_1$ to $C_{18}$ divalent aliphatic hydrocarbon group, a $C_3$ to $C_{13}$ divalent alicyclic hydrocarbon group, and a $C_6$ to $C_{14}$ divalent aromatic hydrocarbon group that does not comprise tetramethylxylylene, wherein a plurality of $L_1$ groups may be identical to or different from one another;

wherein the ratio, based upon the weight of each compound, of the latex compound to the polycarbodiimide compound is in the range from about 50:50 to about 80:20; and wherein the composition comprises from about 10% to about 95%, by weight, based upon the total weight of the composition, of a combined amount of the polycarbodiimide compound and the latex compound, and has at least moderate flexibility when cured.

15. A nail composition according to claim 14, further comprising at least one of a solvent, an adhesive agent, and a secondary film former.

16. A nail composition according to claim 14, wherein the ratio, based upon the weight of each compound, of the latex compound to the polycarbodiimide compound is about 80:20.

17. A nail composition according to claim 14, wherein the ratio, based upon the weight of each compound, of the latex compound to the polycarbodiimide compound is about 70:30.

18. A nail composition according to claim 14, wherein the composition comprises from about 20% to about 40%, by weight, based upon the total weight of the composition, of a combined amount of the polycarbodiimide compound and the latex compound.

19. A nail composition according to claim 14, wherein the composition comprises about 30%, by weight, based upon the total weight of the composition, of a combined amount of the polycarbodiimide compound and the latex compound.

20. A nail composition according to claim 14, wherein the ratio, based upon the weight of each compound, of the latex compound to the polycarbodiimide compound is from about 70:30 to about 80:20, and wherein the composition comprises about 30%, by weight, based upon the total weight of the composition, of a combined amount of the polycarbodiimide compound and the latex compound.

21. A nail composition according to claim 1, wherein $X_1$ and $X_2$, each independently, represents O.

22. A nail composition according to claim 1, wherein $R_1$ and $R_2$, each independently, represent a hydrocarbon group containing one or more catenary or non-catenary hetero-atoms and containing linear or branched and acyclic groups which are ionic or non-ionic segments or a partially or fully fluorinated hydrocarbon group containing one or more catenary or non-catenary hetero-atoms.

23. A nail composition according to claim 1, wherein $R_1$ and $R_2$, each independently, represent a hydrocarbon group containing one or more catenary or non-catenary hetero-atoms and containing linear or branched or acyclic groups.

24. A nail composition according to claim 1, wherein $R_1$ and $R_2$, each independently, is selected from the group consisting of methyl glycolate, methyl lactate, polypropylene glycol, and dialkylamino alcohol.

25. A nail composition according to claim 1, wherein $L_1$ represents a $C_1$ to $C_{18}$ divalent aliphatic hydrocarbon group, a $C_3$ to $C_{13}$ divalent alicyclic hydrocarbon group, or a $C_3$ to $C_{12}$ divalent heterocyclic group.

26. A nail composition according to claim 1, wherein $L_1$ represents a $C_1$ to $C_{18}$ divalent aliphatic hydrocarbon group, or a $C_3$ to $C_{13}$ divalent alicyclic hydrocarbon group.

27. A nail composition according to claim 1, wherein $L_1$ is selected from the group consisting of a diradical of tolylene, hexamethylene, hydrogenated xylylene, xylylene, 2,2,4-trimethylhexamethylene, 1,12-dodecane, norbornane, 2,4-bis-(8-octyl)-1,3-dioctylcyclobutane, 4,4'-di cyclohexylmethane, isophorone, 1,5-naphthylene, 4,4' diphenylmethane, 4,4' diphenyldimethylmethane, and phenylene.

28. A nail composition according to claim 1, wherein the latex compound and the polycarbodiimide are selected to react with a keratinous substrate of a nail.

29. A nail composition according to claim 14, wherein $X_1$ and $X_2$, each independently, represents O.

30. A nail composition according to claim 14 wherein $R_1$ and $R_2$, each independently, represent a hydrocarbon group containing one or more catenary or non-catenary hetero-atoms and containing linear or branched and cyclic or acyclic groups; $L_1$ represents one of a $C_1$ to $C_{18}$ divalent aliphatic hydrocarbon group and a $C_3$ to $C_{13}$ divalent alicyclic hydrocarbon group.

31. A nail composition according to claim 14, wherein $R_1$ and $R_2$, each independently, represent a hydrocarbon group containing one or more catenary or non-catenary hetero-atoms and containing linear or branched or acyclic groups.

32. A nail composition according to claim 14, wherein $R_1$ and $R_2$, each independently, is selected from the group consisting of methyl glycolate, methyl lactate, polypropylene glycol, and dialkylamino alcohol.

33. A nail composition according to claim 14, wherein $R_1$ and $R_2$, are polyethylene glycol monomethyl ether and $L_1$ represents a $C_6$ to $C_{14}$ divalent aromatic hydrocarbon group that does not comprise tetramethylxylylene.

34. A nail composition according to claim 14, wherein $L_1$ represents a $C_1$ to $C_{18}$ divalent aliphatic hydrocarbon group, or a $C_3$ to $C_{13}$ divalent alicyclic hydrocarbon group.

35. A nail composition according to claim 14, wherein $L_1$ is selected from the group consisting of a diradical of tolylene, hexamethylene, hydrogenated xylylene, xylylene, 2,2,4-trimethylhexamethylene, 1,12-dodecane, norbornane, 2,4-bis-(8-octyl)-1,3-dioctylcyclobutane, 4,4'-dicyclohexylmethane, isophorone, 1,5-naphthylene, 4,4' diphenylmethane, 4,4' diphenyldimethylmethane, and phenylene.

36. A nail composition according to claim 14, wherein the latex compound and the polycarbodiimide are selected to react with a keratinous substrate of a nail.

\* \* \* \* \*